(12) United States Patent
Ziegler

(10) Patent No.: US 6,436,981 B1
(45) Date of Patent: Aug. 20, 2002

(54) DIHYDROTRIAZOLONE DERIVATIVES AS PESTICIDES

(75) Inventor: Hugo Ziegler, Witterswil (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/736,694

(22) Filed: Dec. 13, 2000

Related U.S. Application Data

(63) Continuation of application No. PCT/EP99/05216, filed on Jul. 21, 1999.

(30) Foreign Application Priority Data

Jul. 23, 1998 (CH) ............................................. 1559/98

(51) Int. Cl.$^7$ ....................... A01N 43/653; C07D 249/12
(52) U.S. Cl. ......................... 514/384; 514/63; 548/110; 548/263.2; 548/263.6; 548/263.8; 548/264.6
(58) Field of Search .................... 514/63, 384; 548/110, 548/263.2, 263.6, 263.8, 264.6

(56) References Cited

FOREIGN PATENT DOCUMENTS

WO     WO 00/53585    *   9/2000

* cited by examiner

*Primary Examiner*—Patricia L. Morris
(74) *Attorney, Agent, or Firm*—Joseph C. Gil; John E. Mrozinski, Jr.

(57) ABSTRACT

Compounds of formula 1

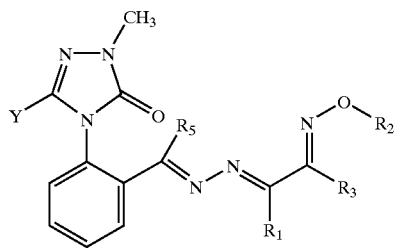

wherein:
- Y signifies halogen, $C_1$–$C_4$-alkoxy, $C_1$–$C_4$-alkylthio or hydroxy;
- $R_1$ signifies methyl, ethyl or cyclopropyl;
- $R_2$ signifies $C_1$–$C_6$-alkyl or $C_1$–$C_6$-alkyl substituted by 1 to 5 fluorine atoms;
- $R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkinyl, $C_2$–$C_6$-alkinyloxy, $C_1$–$C_6$-alkoxycarbonyl or CN, whereby, with the exception of CN, the above-mentioned groups may be substituted by identical or different substituents; or
- $R_3$ is aryl, heteroaryl, heterocyclyl, aryloxy, heteroaryloxy or heterocyclyloxy, whereby the above-mentioned groups may be substituted by identical or different substituents,
- $R_5$ signifies hydrogen or methyl; have microbicidal, insecticidal and acaricidal activity and may be used to control insects and plant-pathogenic fungi in agriculture, horticulture and in the field of hygiene.

9 Claims, No Drawings

DIHYDROTRIAZOLONE DERIVATIVES AS PESTICIDES

This application is a continuation of PCT/EP 99/05216 (published in English as WO 00/05222), filed Jul. 21, 1999 which claims priority to Swiss application CH 1559/98 filed Jul. 23, 1998.

The present invention relates to new dihydrotriazolone derivatives having microbicidal, insecticidal and acaricidal activity, a process for their preparation, new intermediates for the preparation thereof, agrochemical compositions containing these active ingredients, as well as the use thereof in the control and prevention of plant-pathogenic fungi, acarids and insects in agriculture, horticulture and in the field of hygiene.

The new compounds fall within formula I,

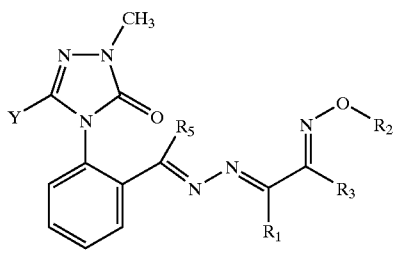

wherein:
Y signifies halogen, $C_1$–$C_4$-alkoxy, $C_1$–$C_4$-alkylthio or hydroxy;
$R_1$ signifies methyl, ethyl or cyclopropyl;
$R_2$ signifies $C_1$–$C_6$-alkyl or $C_1$–$C_6$-alkyl substituted by 1 to 5 fluorine atoms;
$R_3$ signifies $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkinyl, $C_2$–$C_6$-alkinyloxy, $C_1$–$C_6$-alkoxycarbonyl or CN, whereby, with the exception of CN, the above-mentioned groups may be substituted by one or more identical or different substituents selected from the group comprising halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylaminocarbonyl, di-$C_1$–$C_6$-alkylaminocarbonyl, $C_2$–$C_6$-alkenyloxy, $C_3$–$C_6$-cycloalkyl, $C_3$–$C_6$-cycloalkoxy, heterocyclyl, heterocyclyloxy, aryl, aryloxy, heteroaryl, heteroaryloxy, whereby the cyclic radicals in turn may be substituted by one or more identical or different substituents selected from the group comprising halogen, cyano, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted aryl, optionally substituted aryloxy, optionally substituted heteroaryl and optionally substituted heteroaryloxy; or
$R_3$ signifies aryl, heteroaryl, heterocyclyl, aryloxy, hetaryloxy or heterocyclyloxy, whereby the above-mentioned groups may be substituted by one or more identical or different substituents selected from the group comprising halogen, $C_1$–$C_6$-alkyl, $C_1$–$C_6$-alkoxy, halo-$C_1$–$C_6$-alkoxy, halo-$C_1$–$C_6$-alkyl, $C_1$–$C_6$-alkylthio, halo-$C_1$–$C_6$-alkylthio, $C_1$–$C_6$-alkylsulfonyl, halo-$C_1$–$C_6$-alkylsulfinyl, $C_1$–$C_6$-alkyl-sulfonyl, halo-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkylcarbonyl, halogen-$C_1$–$C_6$-alkylcarbonyl, $C_1$–$C_6$-alkoxycarbonyl, halo-$C_1$–$C_6$-alkoxycarbonyl, $C_1$–$C_6$-alkylaminocarbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is mono- to tetra-substituted by $C_1$–$C_4$-alkyl and/or by halogen, or CN, $SF_5$ and $QR_4$;
Q signifies a direct bond, O, O($C_1$–$C_6$-alkylene), ($C_1$–$C_6$-alkylene)O, S(=O)p, S(=O)p($C_1$–$C_6$-alkylene), ($C_1$–$C_6$-alkylene)S(=O)p, $C_1$–$C_8$-alkylene, $C_2$–$C_6$-alkenylene or $C_2$–$C_6$-alkenylene;
$R_4$ signifies an unsubstituted $C_2$–$C_6$-alkenyl- or $C_2$–$C_6$-alkinyl group or one which is substituted by 1 to 3 halogen atoms, a ($C_1$–$C_4$-alkyl)$_3$Si group, whereby the alkyl groups may be identical or different, CN, an unsubstituted or mono- to tetra-substituted $C_3$–$C_6$-cycloalkyl, aryl, heteroaryl or heterocyclyl group, whereby the substituents are selected from the group comprising halogen, $C_1$–$C_6$-alkyl, halo-$C_1$–$C_6$-alkyl, $C_1$–$C_6$-alkoxy, halogen-$C_1$–$C_6$-alkoxy, phenoxy and CN;
p is 0, 1 or 2;
$R_5$ signifies hydrogen or methyl.

Formula I is to include all possible isomeric forms and mixtures thereof, e.g. racemic mixtures and any [E/Z] mixtures.

Alkyl is either straight-chained, i.e. methyl, ethyl, propyl, butyl, pentyl or hexyl, or branched, e.g. isopropyl, isobutyl, sec.-butyl, tert.-butyl, isopentyl, neopentyl or isohexyl.

Alkenyl is either straight-chained, e.g. vinyl, 1-methylvinyl, allyl, 1-butenyl or 2-hexenyl, or branched, e.g. isopropenyl.

Alkinyl is either straight-chained, e.g. propargyl, 2-butinyl or 5-hexinyl, or branched, e.g. 2-ethinylpropyl or 2-propargylisopropyl.

Alkylenedioxy is —O(alkylene)O—.

Alkylene is either straight-chained, e.g. —$CH_2CH_2$—, —$CH_2CH_2CH_2$— or —$CH_2CH_2CH_2CH_2$—, or branched, e.g. —CH($CH_3$)—, —CH($C_2H_5$)—, —C($CH_3$)$_2$—, —CH($CH_3$)$CH_2$— or —CH($CH_3$)CH($CH_3$)—.

Alkenylene is either straight-chained, e.g. vin-1,2-ylene, all-1,3-ylene, but-1-en-1,4-ylene or hex-2-en-1,6-ylene, or branched, e.g. 1-methylvin-1,2-ylene.

Alkinylene is either straight-chained, e.g. propargylene, 2-butinylene or 5-hexinylene, or branched, e.g. 2-ethinylpropylene or 2-propargylisopropylene.

Halogen is fluorine, chlorine, bromine or iodine, preferably fluorine, chlorine or bromine.

Halogenalkyl may contain identical or different halogen atoms.

Aryl signifies phenyl or naphthyl, preferably phenyl.

Heteroaryl signifies a cyclic aromatic group with 5 to 9 ring members in one or two rings, of which 1 to 3 members are hetero atoms selected from the group oxygen, sulphur and nitrogen. 1 to 2 benzene rings may be condensed on the heterocycle, the binding to the residual molecule taking place either through the hetero or the benzene moiety.

Examples are benzimidazolyl, benzisoxazolyl, benzisothiazolyl, benzocumarinyl, benzofuryl, benzothiadiazolyl, benzothiazolyl, benzothienyl, benzoxazolyl, benzoxdiazolyl, quinazolinyl, quinolyl, quinoxalinyl, carbazolyl, dihydrobenzofuryl, furyl, imidazolyl, indazolyl, indolyl, isoquinolinyl, isothiazolyl, isoxazolyl, methylenedioxyphenyl, ethylenedioxyphenyl, naphthyridinyl, oxazolyl, phenanthridinyl, phthalazinyl, pteridinyl, purinyl, pyrazinyl, pyrazolyl, pyridazinyl, pyrazolo[3,4-b]pyridyl, pyridyl, pyrimidinyl, pyrrolyl, tetrazolyl, oxadiazolyl, thiadiazolyl, thiazolyl, thienyl, triazinyl and triazolyl.

Preference is given to pyridyl, pyrazinyl, pyrimidinyl, thiazolyl, quinolinyl and thienyl. Heterocyclyl signifies a 5- to 7-membered, non-aromatic ring with one to three hetero atoms selected from the group comprising N, O and S. Preference is given to non-aromatic 5- and 6-rings that have one nitrogen atom as a hetero atom and optionally one further hetero atom.

Piperidinyl, morpholinyl, pyrrolidinyl, pyrazolinyl, thiazolinyl and oxazolinyl are preferred.

Of the compounds of formula I, those groups are preferred, wherein:

(1) a) Y is chlorine, bromine, hydroxy, methoxy, or methylthio; or
  b) $R_1$ is methyl; or
  c) $R_2$ is methyl, ethyl, fluoromethyl or trifluoroethyl, preferably methyl; or
  d) $R_3$ is $C_1$–$C_6$-alkyl, $C_1$–$C_6$-alkoxy, $C_2$–$C_6$-alkenyl, $C_2$–$C_6$-alkenyloxy, $C_2$–$C_6$-alkinyl, $C_3$–$C_6$-alkinyloxy, $C_3$–$C_6$-cycloalkyl, $C_3$–$C_6$-cycloalkyloxy or $C_1$–$C_6$-alkoxycarbonyl, whereby the above-mentioned groups may be partially or totally halogenated; also CN, OCN or halogen; or
  e) $R_3$ is phenyl which is unsubstituted or mono- to tri-substituted by identical or different substituents from halogen, $C_1$–$C_6$-alkyl, $C_1$–$C_6$-halogenalkyl, $C_1$–$C_6$-alkoxy, $C_1$–$C_6$-haloalkoxy, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkoxycarbonyl, CN, OCN; optionally substituted benzyl, optionally substituted phenyl, or optionally substituted phenoxy; or
  f) $R_3$ is pyridyl, pyrimidinyl, furyl, thienyl, oxazolyl, isoxazolyl, thiazolyl, isothiazolyl, imidazolyl, pyrazolyl, which are unsubstituted or mono- to trisubstituted by identical or different substituents from halogen, cyano, nitro, aminocarbonyl, $C_1$–$C_4$-alkyl, $C_1$–$C_4$-haloalkyl, $C_1$–$C_4$-alkylcarbonyl, $C_1$–$C_4$-alkylsulfonyl, $C_1$–$C_6$-alkylsulfoxyl, $C_3$–$C_6$-cycloalkyl, optionally substituted arylcarbonyl, $C_1$–$C_4$-alkoxy, $C_1$–$C_4$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, or $C_2$–$C_6$-alkenyl; or
  g) $R_5$ is hydrogen.

(2) compounds of formula I, wherein:
  Y is $C_1$–$C_4$-alkoxy, preferably methoxy, or halogen, preferably chlorine;
  $R_1$ is methyl or ethyl, preferably methyl;
  $R_2$ is $C_1$–$C_6$-alkyl or $C_1$–$C_6$-alkyl substituted by 1 to 5 fluorine atoms;
  $R_3$ is $C_1$–$C_6$alkyl, $C_1$–$C_6$-alkoxy, $C_1$–$C_6$-alkoxycarbonyl, CN, $C_3$–$C_6$-cycloalkyl, aryl, heeroaryl, heterocyclyl, aryloxy, heteroaryloxy or heterocyclyloxy, whereby, with the exception of CN, the above-mentioned groups may be substituted;
  $R_5$ is hydrogen or methyl.

(2a) Of those mentioned under (2), especially those in which:
  $R_2$ is $C_1$–$C_6$-alkyl, fluoromethyl, difluoromethyl or 2,2,2-trifluoroethyl;
  $R_3$ is $C_1$–$C_6$alkyl, $C_1$–$C_6$-alkoxy, $C_1$–$C_6$-alkoxycarbonyl, CN, $C_3$–$C_6$-cycloalkyl, phenyl which is unsubstituted or mono- to tri-substituted by halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkenyl, $C_2$–$C_4$-alkenyloxy, $C_2$–$C_6$-alkinyl, $C_3$–$C_6$-alkinyloxy, CN, OCN, benzyl, phenyl, or phenyloxy, wherein these aromatic groups are unsubstituted or mono- or disubstituted by halogen, $C_1$–$C_2$-alkyl, $C_1$–$C_2$-haloalkyl or $C_1$–$C_2$-alkoxy.

(2b) Of those mentioned under (2a), especially those in which:
  $R_3$ is $C_1$–$C_4$-alkyl or phenyl, which is unsubstituted or mono- to disubstituted by halogen, $C_1$–$C_2$-alkyl, $C_1$–$C_2$-haloalkyl, $C_1$–$C_2$-alkoxy.

(3) compounds of formula I, wherein:
  Y is methoxy;
  $R_1$ is methyl, ethyl or cyclopropyl, preferably methyl;
  $R_2$ is $C_1$–$C_6$-alkyl, preferably methyl;
  $R_3$ is $C_1$–$C_6$-alkyl, $C_1$–$C_6$-haloalkyl, $C_2$–$C_6$-alkenyl, $C_1$–$C_6$-alkoxy, $C_2$–$C_6$-alkynyloxy, $C_1$–$C_6$-alkoxycarbonyl, CN, $C_3$–$C_6$-cycloalkyl, aryl, heteroaryl, heterocyclyl, aryloxy, heteroaryloxy or heterocyclyloxy, whereby the hydrocarbon radicals and the cyclic radicals may be substituted as mentioned above;
  $R_5$ is hydrogen or methyl.

(3a) Of those mentioned under (3), especially those in which:
  $R_3$ is $C_1$–$C_6$-alkyl, $C_1$–$C_6$-haloalkyl, $C_2$–$C_6$-alkenyl, $C_1$–$C_6$-alkoxy, $C_2$–$C_6$-alkynyloxy, $C_1$–$C_6$-alkoxycarbonyl, $C_3$–$C_6$-cycloalkyl.

(3b) Of those mentioned under (3), also especially those in which:
  $R_3$ is phenyl that is unsubstituted or mono- or disubstituted by halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkenyl, $C_2$–$C_4$-alkenyloxy, benzyl, phenyl, or phenyloxy, wherein these aromatic groups are unsubstituted or mono- or disubstituted by halogen, $C_1$–$C_2$-alkyl, $C_1$–$C_2$-haloalkyl or $C_1$–$C_2$-alkoxy.

Compounds of formula I may be produced as follows:

A) A compound of formula I is produced whereby a hydrazone of the general formula II

II wherein $R_1$, $R_2$ and $R_3$ have the significances given for formula I, is reacted with an aldehyde or a ketone of the general formula III or with one of its acetal derivatives of the general formula IV

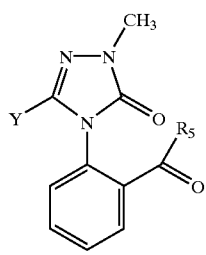

III

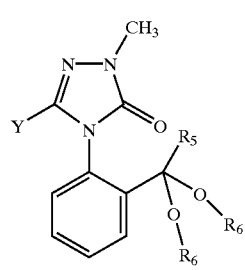

IV wherein Y and $R_5$ have the significances given for formula I and $R_6$ signifies $C_1$–$C_6$-alkyl or the two $R_6$, together with the two oxygen atoms and the carbon to which they are bonded, signify a cyclic acetal.

A compound of formula III is produced whereby a compound of formula XV

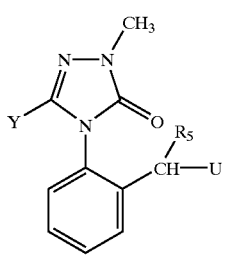

XV wherein Y and $R_5$ have the significances given for formula I and U is a leaving group, for example chlorine, bromine, iodine, mesyloxy, benzenesulphonyloxy or tosyloxy, is firstly hydrolysed to form the corresponding benzyl alcohol and then oxidised, e.g. with chromic acid, atmospheric oxygen, N-bromosuccinimide, $MnO_2$, $SeO_2$, $Cl_2$, $Br_2$, by means of catalytic dehydrogenation or by Oppenauer oxidation.

Compounds of formula XV are known, e.g. from WO 97/02255.

Compounds of formula III may be acetalised by known methods to compounds of formula IV by means of an acid-catalysed reaction with a corresponding alcohol.

B) A compound of formula I is produced whereby a hydrazone of the general formula V,

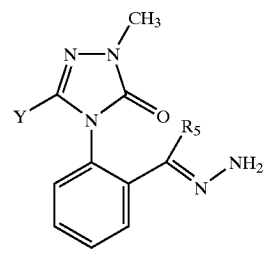

V wherein Y and $R_5$ have the significances given under formula I, is reacted with an aldehyde or a ketone of the general formula VI

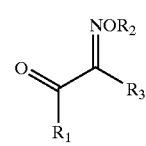

VI wherein $R_1$, $R_2$, and $R_3$ have the significances given for formula I.

The compounds of formula V may be obtained by reacting a compound of formula III with hydrazine.

C) A compound of formula I is produced whereby an oxime of the general formula VII

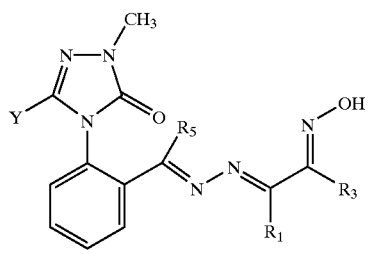

VII wherein Y, $R_1$, $R_3$, and $R_5$ have the significances given for formula I, is etherified.

The compounds of formula VII may be obtained whereby either a) a ketone of the general formula VIII

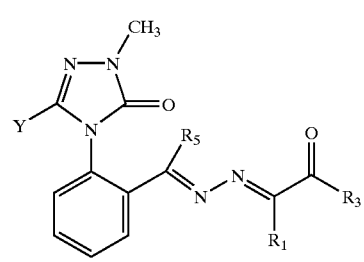

VIII wherein Y, $R_1$, $R_3$ and $R_5$ have the significances given for formula I, is reacted with hydroxylamine or with one of its salts, or b) a compound of the general formula IX,

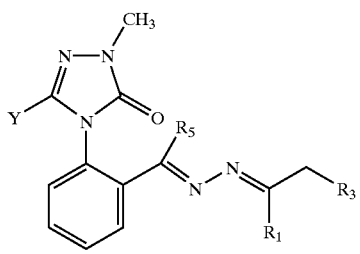

IX wherein Y, $R_1$, $R_3$ and $R_5$ have the significances given for formula I, is reacted with nitrous acid or with an alkyl nitrite in the presence of an acid or base, or c) a hydrazone of the general formula X

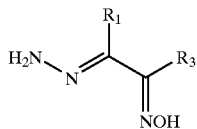

X wherein $R_1$ and $R_3$ have the significances given for formula I, is reacted with an aldehyde of the general formula III or with an acetal of the general formula IV, as described under A), or d) a ketone-oxime of the general formula XI

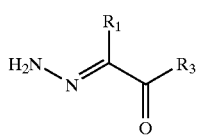

XI wherein $R_1$ and $R_3$ have the significances given for formula I, is reacted with a hydrazone of the general formula V.

Compounds of formulae VIII and IX may be produced by reacting an aldehyde or a ketone of formula III with the corresponding hydrazone of formula XIV or XV

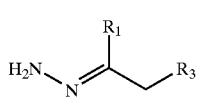

XIV

XV wherein $R_1$ and $R_3$ have the significances given for formula I.

D) A compound of formula I may be produced whereby a ketone of the general formula VIII is reacted with an alkoxyamine of the general formula XII $$R_2-ONH_2$$

XII wherein $R_2$ has the significances given for formula I, or with one of its salts.

E) A compound of formula I, wherein Y is $C_1$–$C_4$-alkoxy or $C_1$–$C_4$-alkylthio, may be produced whereby a halide of the general formula XII

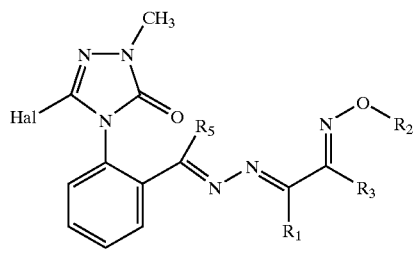

XIII wherein Hal is chlorine or bromine, and $R_1$, $R_2$, $R_3$ and $R_5$ have the significances given for formula I, is reacted with a $C_1$–$C_4$-alcoholate, such as sodium methylate, or with a $C_1$–$C_4$-thiolate, such as sodium ethyl thiolate.

F) A compound of formula I, wherein Y is hydroxy, may be produced whereby a halide of the general formula XIII

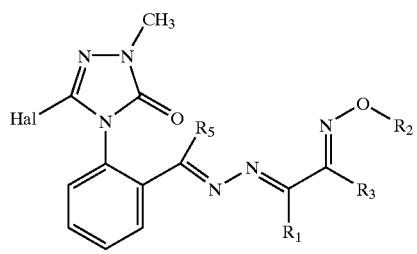

XIII undergoes either acidic or basic hydrolysis.

All the above-described reactions and educts are known per se.

The new, above-mentioned intermediates similarly form an object of this invention. Those of formulae II, IV, V, VII, VIII and IX are of particular significance.

The compounds of formula I are of preventive and/or curative merit as active ingredients for the control of plant pests and may be used in the agricultural sector and related fields The active ingredients of formula I according to the invention are notable for their good activity even at low concentrations, for their good plant tolerance and for their environmental acceptability. They possess very advantageous, especially systemic properties, and may be used for the protection of numerous cultivated plants. Using the active ingredients of formula I, pests appearing on plants or plant parts (fruits, flowers, foliage, stems, tubers, roots) of different crops can be checked or destroyed, whereby parts of the plant which grow later are also protected e.g. from phytopathogenic micro-organisms.

The compounds of formula I may also be employed as a dressing for seeds (fruits, tubers, grain) and plant cuttings to protect against fungal infections, and to protect against phytopathogenic fungi appearing in the soil.

Compounds I are effective for example against the phytopathogenic fungi belonging to the following classes: *Fungi imperfecti* (e.g. Botrytis, Pyricularia, Helminthosporium, Fusarium, Septodia, Cercospora and Altemaria); Basidiomycetes (e.g. Rhizoctonia, Hemileia, Puccinia); Ascomycetes (e.g. Venturia and Erysiphe, Podosphaera, Monilinia, Uncinula) and Oomycetes (e.g. Phytophthora, Pythium, Plasmopara).

Target cultivations for the plant-protecting usage in the context of the invention are, for example, the following species of plant: cereals, (wheat, barley, rye, oats, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybean); oleaginous fruits (rape, mustard, poppy, olives, sunflowers, coconut, castor oil plants, cocoa beans, groundnuts); cucumber plants (squashes, cucumbers, melons); fibrous plants (cotton, flax, hemp or jute); citrus fruits (oranges, lemons, grapefruit, mandarins); vegetables (spinach, lettuce, asparagus, cabbages, carrots, onions, tomatoes, potatoes, paprika); Lauraceae (avocado, cinnamon, camphor); and plants such as tobacco, nuts, coffee, aubergines, sugar cane, tea, pepper, vines, hops, banana plants, natural rubber plants and ornamentals.

In addition, the compounds of formula I according to the invention are valuable active ingredients against insects and pests of the order Acarina, such as those appearing on crop plants and ornamentals in agriculture and horticulture and in forestry, whilst being tolerated well by warm-blooded animals, fish and plants. The compounds of formula I are especially suitable for controlling pests in cultivations of cotton, vegetables, fruit and rice, such as spider mites, aphids, caterpillars and plant and leaf hoppers in rice. The pests that are primarily controlled are spider mites such as *Panonychus ulmi*, aphids such as *Aphis craccivora*, caterpillars such as those of *Heliothis virescens* and plant and leaf hoppers in rice, such as *Nilaparvata lugens* or *Nephotettix cincticeps*.

The good pesticidal activity of the compounds I according to the invention corresponds to a mortality rate of at least 50–60% of the pests mentioned.

Further fields of application for the active ingredients according to the invention are the protection of stock and material, where the goods stored are protected against rotting and mildew, as well as against animal pests (e.g. grain weevils, mites, maggots, etc). In the hygiene sector, compounds of formula I provide successful control of animal parasites such as ticks, mites, warble flies etc., on domestic animals and productive livestock. Compounds I are effective against individual or all stages of development of pests showing normal sensitivity, and also of those showing resistance Their activity may be demonstrated, for example, by the mortality of the pests, which occurs immediately or only after some time, for example during a moult, or by reduced egg laying and/or hatching rate.

Compounds I are used in this instance in unmodified form or preferably together with the excipients that are usual in formulation technology. To this end, they are suitably processed in known manner e.g. into emulsifiable concentrates, coatable pastes, directly sprayable or dilutable solutions, diluted emulsions, wettable powders, soluble powders, dusts or granules, e.g. by encapsulation in e.g. polymeric substances. As with the type of compositions, the methods of application, such as spraying, atomizing, dusting, scattering, coating or pouring, are selected in accordance with the intended objectives and the prevailing circumstances. Suitable carriers and additives may be solid or liquid and are substances that are appropriate in formulation technology, for example natural or regenerated mineral substances, solvents, dispersants, wetting agents, tackifiers, thickeners, binding agents or fertilisers.

The compounds of formula I may be mixed with further active ingredients, e.g. fertilisers, trace element intermediates or other plant-protecting compositions, especially with further fungicides. Unexpected synergistic effects may thus occur.

Preferred mixture components are:

Azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole, triticonazole; pyrimidinyl carbinols, such as ancymidol, fenarimol, nuarimol; 2-amino-pyrimidines, such as bupirimate, dimethirimol, ethirimol; morpholines, such as dodemorph, fenpropidin, fenpropimorph, spiroxamin, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozolin; carboxamides, such as carboxin, fenfuram, flutolanil, mepronil, oxycarboxin, thifluzamide; guanidines, such as guazatine, dodine, iminoctadine; strobilurines, such as azoxystrobin, kresoxime-methyl, SSF-126 (metominostrobin or fenominostrobin), SSF-129 (α-methoximino-N-methyl-2-[(2,5-dimethylphenoxy)methyl]-benzeneacetamide), trifloxystrobin (2-[α-{[(α-methyl-3-trifluoromethyl-benzyl)imino]-oxy}-o-tolyl]-glyoxylic acid methylester-O-methyloxime); dithiocarbamates, such as ferbam, mancozeb, maneb, metiram, propineb, thiram, zineb, ziram; N-halomethylthioamides, such as captafol, captan, dichlofluanid, fluoromide, folpet, tolyfluanid; Cu compounds, such as Bordeaux mixture, copper hydroxide, copper oxychloride, copper sulfate, cuprous oxide, mancopper, oxine-copper; nitrophenol derivatives, such as dinocap, nitrothal-isopropyl; organo-P derivatives, such as edifenphos, iprobenphos, isoprothiolane, phosdiphen, pyrazophos, tololofos-methyl; miscellaneous, such as acibenzolar-S-methyl, anilazine, blasticidin-S, quinomethionat, chloroneb, chlorothalonil, cymoxanil, dichlone, diclomezine, dicloran, diethofencarb, dimethomorph, dithianon, etridiazole, famoxadone, fentin, fenamidon, ferimzone, fluazinam, flusulfamide, fenhexamid, fosetyl-aluminium, hymexazol, kasugamycin, iprovalicarb, IKF-916, methasulfocarb, pencycuron, phthalide, polyoxins, probenazole, propamocarb, pyroquilon, quinoxyfen, quintozene, sulfur, triazoxide, tricyclazole, triforine, validamycin.

One preferred method of applying an active ingredient of formula I or an agrochemical composition containing at least one of these active ingredients is application to the foliage (leaf application). The frequency and rate of application depend on the severity of infestation by the invader in question. However, the active ingredients I can also penetrate the plant through the roots via the soil (systemic action) by drenching the locus of the plants with a liquid preparation, or by applying the substances to the soil in solid form, for example in granular form (soil application). With paddy rice cultures, granules may be metered into the flooded paddy field. The compounds I may also be applied to seed grain for seed pre-treatment (coating) by either drenching the grains or tubers in a liquid preparation of the active ingredient or coating them with a solid preparation.

The compositions are prepared in known manner, e.g. by intimately mixing and/or grinding the active ingredient with extenders, such as solvents, solid carriers and optionally surface-active compounds (surfactants).

The agrochemical compositions normally contain 0.1 to 99 percent by weight, especially 0.1 to 95 percent by weight, of active ingredient of formula I, 99.9 to 1 percent by weight, especially 99.8 to 5 percent by weight, of a solid or liquid additive and 0 to 25 percent by weight, especially 0.1 to 25 percent by weight, of a surfactant.

Favourable application rates generally lie between 1 g and 2 kg of active substance (AS) per hectare (ha), preferably between 10 g and 1 kg AS/ha, especially between 20 g and 600 g AS/ha.

For usage as a seed dressing, the dosages advantageously used are 10 mg to 1 g of active substance per kg seeds.

Whereas it is preferred to formulate commercial products as concentrates, the end user will normally use dilute formulations.

The compositions may also contain further additives, such as stabilisers, anti-foaming agents, viscosity regulators, binding agents or tackifiers, as well as fertilisers or other active ingredients, in order to achieve special effects.

PREPARATION EXAMPLE 5-methoxy-4-(2-{[2-Methoxyimino-1-methyl-2-(3-trifluoromethyl-phenyl)-ethylidene]-hydrazonomethyl}-phenyl)-2-methyl-2,4-dihydro-[1,2,4]triazol-3-one A solution of 1.17 g of 2-(3-methoxy-1-methyl-5-oxo-1,5-dihydro-[1,2,4]triazol-4-yl)-benzaldehyde and 1.43 g of 2-hydrazono-1-(3-trifluoromethyl-phenyl)-propan-1-one-O-methyl-oxime in 10 ml of methanol is held at reflux temperature for 4 hours. After cooling to 5° C., filtration takes place, and the filtrate is concentrated by evaporation on a rotary evaporator. The residue is chromatographed on silica gel using ethyl acetate/hexane (1:1). The title compound is thus obtained as a yellow crystal powder having a melting point of 157–161° C. in the form of an isomeric mixture in a ratio of ca. 2:1.

The compounds of the following tables may be produced in analogous manner.

TABLE 1

Compounds of the general formula I.1, in which Y signifies methoxy, $R_2$ signifies methyl and $R_5$ signifies hydrogen and $R_3$ corresponds in each case to one line of Table A.

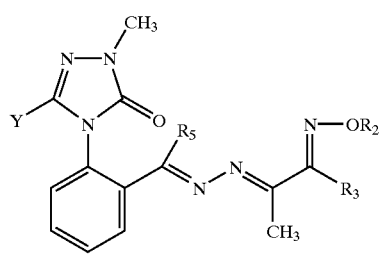

I.1

TABLE 2

Compounds of the general formula I.1, in which Y signifies chlorine, $R_2$ signifies methyl and $R_5$ signifies hydrogen and $R_3$ corresponds in each case to one line of Table A.

TABLE 3

Compounds of the general formula I.1, in which Y signifies methoxy, $R_2$ signifies ethyl and $R_5$ signifies hydrogen and $R_3$ corresponds in each case to one line of Table A.

TABLE 4

Compounds of the general formula I.1, in which Y signifies chlorine, $R_2$ signifies ethyl and $R_5$ signifies hydrogen and $R_3$ corresponds in each case to one line of Table A.

TABLE 5

Compounds of the general formula I.1, in which Y signifies methylthio, $R_2$ signifies methyl and $R_5$ signifies hydrogen and $R_3$ corresponds in each case to one line of Table A.

TABLE 6

Compounds of the general formula I.1, in which Y signifies methylthio, $R_2$ signifies ethyl and $R_5$ signifies hydrogen and $R_3$ corresponds in each case to one line of Table A.

TABLE 7

Compounds of the general formula I.1, in which Y signifies methoxy, $R_2$ signifies fluoromethyl and $R_5$ signifies hydrogen and $R_3$ corresponds in each case to one line of Table A.

TABLE 8

Compounds of the general formula I.1, in which Y signifies methoxy, $R_2$ signifies difluoromethyl and $R_5$ signifies hydrogen and $R_3$ corresponds in each case to one line of Table A.

TABLE 9

Compounds of the general formula I.1, in which Y signifies methoxy, $R_2$ signifies 2,2,2-trifluoroethyl and $R_5$ signifies hydrogen and $R_3$ corresponds in each case to one line of Table A.

TABLE 10

Compounds of the general formula I.1, in which Y signifies chlorine, $R_2$ signifies fluoromethyl and $R_5$ signifies hydrogen and $R_3$ corresponds in each case to one line of Table A.

TABLE 11

Compounds of the general formula I.1, in which Y signifies chlorine, $R_2$ signifies difluoromethyl and $R_5$ signifies hydrogen and $R_3$ corresponds in each case to one line of Table A.

TABLE 12

Compounds of the general formula I.1, in which Y signifies chlorine, $R_2$ signifies 2,2,2-trifluoroethyl and $R_5$ signifies hydrogen and $R_3$ corresponds in each case to one line of Table A.

TABLE 13

Compounds of the general formula I.2, in which Y signifies methoxy, $R_2$ signifies methyl and $R_5$ signifies hydrogen and $R_3$ corresponds in each case to one line of Table A.

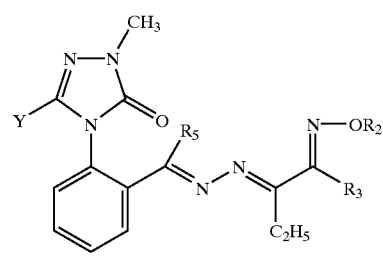

I.2

TABLE 14

Compounds of the general formula I.2, in which Y signifies chlorine, $R_2$ signifies methyl and $R_5$ signifies hydrogen and $R_3$ corresponds in each case to one line of Table A.

TABLE 15

Compounds of the general formula I.3, in which Y signifies methoxy, $R_2$ signifies methyl and $R_5$ signifies hydrogen and $R_3$ corresponds in each case to one line of Table A.

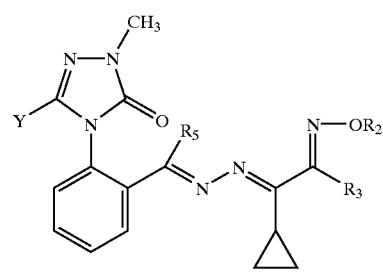

I.3

TABLE 16

Compounds of the general formula I.3, in which Y signifies chlorine, $R_2$ signifies methyl and $R_5$ signifies hydrogen and $R_3$ corresponds in each case to one line of Table A.

TABLE 17

Compounds of the general formula I.2, in which Y signifies methylthio, $R_2$ signifies methyl and $R_5$ signifies hydrogen and $R_3$ corresponds in each case to one line of Table A.

TABLE 18

Compounds of the general formula I.3, in which Y signifies methylthio, $R_2$ signifies methyl and $R_5$ signifies hydrogen and $R_3$ corresponds in each case to one line of Table A.

TABLE 19

Compounds of the general formula I.1, in which Y signifies methoxy, $R_2$ signifies methyl and $R_5$ signifies methyl and $R_3$ corresponds in each case to one line of Table A.

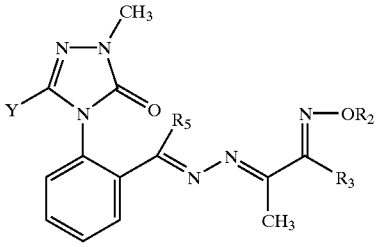

I.1

TABLE 20

Compounds of the general formula I.1, in which Y signifies chlorine, $R_2$ signifies methyl and $R_5$ signifies methyl and $R_3$ corresponds in each case to one line of Table A.

TABLE 21

Compounds of the general formula I.1, in which Y signifies methoxy, $R_2$ signifies ethyl and $R_5$ signifies methyl and $R_3$ corresponds in each case to one line of Table A.

TABLE 22

Compounds of the general formula I.1, in which Y signifies chlorine, $R_2$ signifies ethyl and $R_5$ signifies methyl and $R_3$ corresponds in each case to one line of Table A.

TABLE 23

Compounds of the general formula I.1, in which Y signifies methylthio, $R_2$ signifies methyl and $R_5$ signifies methyl and $R_3$ corresponds in each case to one line of Table A.

TABLE 24

Compounds of the general formula I.1, in which Y signifies methylthio, $R_2$ signifies ethyl and $R_5$ signifies methyl and $R_3$ corresponds in each case to one line of Table A.

TABLE 25

Compounds of the general formula I.1, in which Y signifies methoxy, $R_2$ signifies fluoromethyl and $R_5$ signifies methyl and $R_3$ corresponds in each case to one line of Table A.

TABLE 26

Compounds of the general formula I.1, in which Y signifies methoxy, $R_2$ signifies difluoromethyl and $R_5$ signifies methyl and $R_3$ corresponds in each case to one line of Table A.

TABLE 27

Compounds of the general formula I.1, in which Y signifies methoxy, $R_2$ signifies 2,2-trifluoroethyl and $R_5$ signifies methyl and $R_3$ corresponds in each case to one line of Table A.

TABLE 28

Compounds of the general formula I.1, in which Y signifies chlorine, $R_2$ signifies fluoromethyl and $R_5$ signifies methyl and $R_3$ corresponds in each case to one line of Table A.

TABLE 29

Compounds of the general formula I.1, in which Y signifies chlorine, $R_2$ signifies difluoromethyl and $R_5$ signifies methyl and $R_3$ corresponds in each case to one line of Table A.

TABLE 30

Compounds of the general formula I.1, in which Y signifies chlorine, $R_2$ signifies 2,2,2-trifluoroethyl and $R_5$ signifies methyl and $R_3$ corresponds in each case to one line of Table A.

TABLE 31

Compounds of the general formula I.2, in which Y signifies methoxy, $R_2$ signifies methyl and $R_5$ signifies methyl and $R_3$ corresponds in each case to one line of Table A.

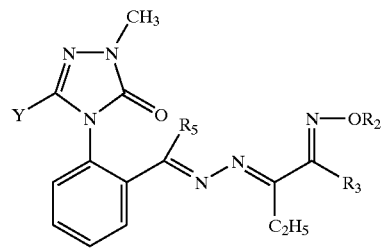

I.2

TABLE 32

Compounds of the general formula I.2, in which Y signifies chlorine, $R_2$ signifies methyl and $R_5$ signifies methyl and $R_3$ corresponds in each case to one line of Table A.

TABLE 33

Compounds of the general formula I.3, in which Y signifies methoxy, $R_2$ signifies methyl and $R_5$ signifies methyl and $R_3$ corresponds in each case to one line of Table A.

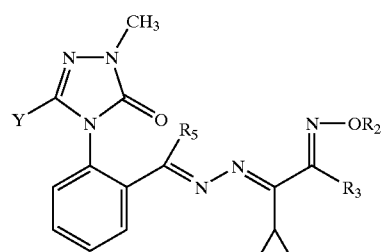

I.3

TABLE 34

Compounds of the general formula I.3, in which Y signifies chlorine, $R_2$ signifies methyl and $R_5$ signifies methyl and $R_3$ corresponds in each case to one line of Table A.

TABLE 35

Compounds of the general formula I.2, in which Y signifies methylthio, $R_2$ signifies methyl and $R_5$ signifies methyl and $R_3$ corresponds in each case to one line of Table A.

TABLE 36

Compounds of the general formula I.3, in which Y signifies methylthio, $R_2$ signifies methyl and $R_5$ signifies methyl and $R_3$ corresponds in each case to one line of Table A.

TABLE A

| No. | $R_3$ |
|---|---|
| 1. | $CH_3$ |
| 2. | $CH_2CH_3$ |
| 3. | $(CH_2)_2CH_3$ |
| 4. | $(CH_2)_3CH_3$ |
| 5. | $(CH_2)_4CH_3$ |
| 6. | $(CH_2)_5CH_3$ |
| 7. | $CH(CH_3)_2$ |
| 8. | $C(CH_3)_3$ |
| 9. | $CH_2CH(CH_3)_2$ |
| 10. | $CH(CH_3)CH_2CH_3$ |
| 11. | $OCH_3$ |
| 12. | $OCH_2CH_3$ |
| 13. | $O(CH_2)_2CH_3$ |
| 14. | $O(CH_2)_3CH_3$ |
| 15. | $O(CH_2)_4CH_3$ |
| 16. | $OCH(CH_3)_2$ |
| 17. | $OCH(CH_3)CH_2CH_3$ |
| 18. | $OC(CH_3)_3$ |
| 19. | $CH=CH_2$ |
| 20. | $CH=CHCH_3$ |
| 21. | $CH=C(CH_3)_2$ |
| 22. | $CH_2CH=CH_2$ |
| 23. | $CH_2CH=CHCH_3$ |
| 24. | $OCH_2CH=CH_2$ |
| 25. | $C\equiv CH$ |
| 26. | $C\equiv CCH_3$ |
| 27. | $C\equiv CC(CH_3)_3$ |
| 28. | $CH_2C\equiv CH$ |
| 29. | $CH_2C\equiv CCH_3$ |
| 30. | $OCH_2C\equiv CH_3$ |
| 31. | $OCH_2C\equiv C-C(CH_3)_3$ |
| 32. | $C(O)OCH_3$ |
| 33. | $C(O)OCH_2CH_3$ |
| 34. | $C(O)O(CH_2)_2CH_3$ |
| 35. | $C(O)O(CH_2)_3CH_3$ |
| 36. | $C(O)O(CH_2)_4CH_3$ |
| 37. | $C(O)OCH(CH_3)_2$ |
| 38. | $C(O)OC(CH_3)_3$ |
| 39. | CN |
| 40. | Cl |
| 41. | Br |
| 42. | $CF_3$ |
| 43. | $CH_2CF_3$ |
| 44. | $CH_2CH_2F$ |
| 45. | $CH_2CN$ |
| 46. | $CH_2OCH_3$ |
| 47. | $CH_2OCH_2CH_3$ |
| 48. | $(CH_2)_2COOCH_3$ |
| 49. | $(CH_2)_2CONH_2$ |
| 50. | $(CH_2)_2CONHCH_3$ |
| 51. | $(CH_2)_2CON(CH_3)_2$ |
| 52. | $(CH_2)_2SCH_3$ |

TABLE A-continued

| No. | R$_3$ |
|---|---|
| 53. | CH$_2$OCH$_2$CH=CH$_2$ |
| 54. | 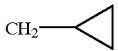 |
| 55. | 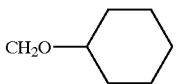 |
| 56. | CH=CF$_2$ |
| 57. | C≡C—Br |
| 58. | C≡C—OCH$_3$ |
| 59. | Cyclopropyl |
| 60. | Cyclobutyl |
| 61. | Cyclopentyl |
| 62. | Cyclohexyl |
| 63. | Phenyl |
| 64. | 1-Naphthyl |
| 65. | 2-Naphthyl |
| 66. | 2-F—C$_6$H$_4$ |
| 67. | 3-F—C$_6$H$_4$ |
| 68. | 4-F—C$_6$H$_4$ |
| 69. | 2,3-F$_2$—C$_6$H$_3$ |
| 70. | 2,4-F$_2$—C$_6$H$_3$ |
| 71. | 2,5-F$_2$—C$_6$H$_3$ |
| 72. | 2,6-F$_2$—C$_6$H$_3$ |
| 73. | 3,4-F$_2$—C$_6$H$_3$ |
| 74. | 3,5-F$_2$—C$_6$H$_3$ |
| 75. | 2-Cl—C$_6$H$_4$ |
| 76. | 3-Cl—C$_6$H$_4$ |
| 77. | 4-Cl—C$_6$H$_4$ |
| 78. | 2,3-Cl$_2$—C$_6$H$_3$ |
| 79. | 2,4-Cl$_2$—C$_6$H$_3$ |
| 80. | 2,5-Cl$_2$—C$_6$H$_3$ |
| 81. | 2,6-Cl$_2$—C$_6$H$_3$ |
| 82. | 3,4-Cl$_2$—C$_6$H$_3$ |
| 83. | 3,5-Cl$_2$—C$_6$H$_3$ |
| 84. | 2,3,4-Cl$_3$—C$_6$H$_2$ |
| 85. | 2,3,5-Cl$_3$—C$_6$H$_2$ |
| 86. | 2,3,6-Cl$_3$—C$_6$H$_2$ |
| 87. | 2,4,5-Cl$_3$—C$_6$H$_2$ |
| 88. | 2,4,6-Cl$_3$—C$_6$H$_2$ |
| 89. | 3,4,5-Cl$_3$—C$_6$H$_2$ |
| 90. | 2-Br—C$_6$H$_4$ |
| 91. | 3-Br—C$_6$H$_4$ |
| 92. | 4-Br—C$_6$H$_4$ |
| 93. | 2,3-Br$_2$—C$_6$H$_3$ |
| 94. | 2,4-Br$_2$—C$_6$H$_3$ |
| 95. | 2,5-Br$_2$—C$_6$H$_3$ |
| 96. | 2,6-Br$_2$—C$_6$H$_3$ |
| 97. | 3,4-Br$_2$—C$_6$H$_3$ |
| 98. | 3,5-Br$_2$—C$_6$H$_3$ |
| 99. | 2-F-3-Cl—C$_6$H$_3$ |
| 100. | 2-F-4-Cl—C$_6$H$_3$ |
| 101. | 2-F-5-Cl—C$_6$H$_3$ |
| 102. | 2-F-3-Br—C$_6$H$_3$ |
| 103. | 2-F-4-Br—C$_6$H$_3$ |
| 104. | 2-F-5-Br—C$_6$H$_3$ |
| 105. | 2-Cl-3-Br—C$_6$H$_3$ |
| 106. | 2-Cl-3-Br—C$_6$H$_3$ |
| 107. | 2-Cl-5-Br—C$_6$H$_3$ |
| 108. | 3-F-4-Cl—C$_6$H$_3$ |
| 109. | 3-F-5-Cl—C$_6$H$_3$ |
| 110. | 3-F-6-Cl—C$_6$H$_3$ |
| 111. | 3-F-4-Br—C$_6$H$_3$ |
| 112. | 3-F-5-Br—C$_6$H$_3$ |
| 113. | 3-F-6-Br—C$_6$H$_3$ |
| 114. | 3-Cl-4-Br—C$_6$H$_3$ |
| 115. | 3-Cl-5-Br—C$_6$H$_3$ |
| 116. | 3-Cl-6-Br—C$_6$H$_3$ |
| 117. | 4-F-5-Cl—C$_6$H$_3$ |
| 118. | 4-F-6-Cl—C$_6$H$_3$ |
| 119. | 4-F-5-Br—C$_6$H$_3$ |
| 120. | 4-F-6-Br—C$_6$H$_3$ |
| 121. | 4-Cl-5-Br—C$_6$H$_3$ |
| 122. | 5-F-6-Cl—C$_6$H$_3$ |
| 123. | 5-F-6-Br—C$_6$H$_3$ |
| 124. | 5-Cl-6-Br—C$_6$H$_3$ |
| 125. | 3-Br-4-Cl-5-Br—C$_6$H$_2$ |
| 126. | 2-CN—C$_6$H$_4$ |
| 127. | 3-CN—C$_6$H$_4$ |
| 128. | 4-CN—C$_6$H$_4$ |
| 129. | 3-OCN—C$_6$H$_4$ |
| 130. | 4-OCN—C$_6$H$_4$ |
| 131. | 2-CH$_3$O—C$_6$H$_4$ |
| 132. | 3-CH$_3$O—C$_6$H$_4$ |
| 133. | 4-CH$_3$O—C$_6$H$_4$ |
| 134. | 2,3-(CH$_3$O)$_2$—C$_6$H$_3$ |
| 135. | 2,4-(CH$_3$O)$_2$—C$_6$H$_3$ |
| 136. | 2,5-(CH$_3$O)$_2$—C$_6$H$_3$ |
| 137. | 3,4-(CH$_3$O)$_2$—C$_6$H$_3$ |
| 138. | 3,5-(CH$_3$O)$_2$—C$_6$H$_3$ |
| 139. | 3,4,5-(CH$_3$O)$_3$—C$_6$H$_2$ |
| 140. | 2-C$_2$H$_5$O—C$_6$H$_4$ |
| 141. | 3-C$_2$H$_5$O—C$_6$H$_4$ |
| 142. | 4-C$_2$H$_5$O—C$_6$H$_4$ |
| 143. | 2-(n-C$_3$H$_7$O)—C$_6$H$_4$ |
| 144. | 3-(n-C$_3$H$_7$O)—C$_6$H$_4$ |
| 145. | 4-(n-C$_3$H$_7$O)—C$_6$H$_4$ |
| 146. | 2-(i-C$_3$H$_7$O)—C$_6$H$_4$ |
| 147. | 3-(i-C$_3$H$_7$O)—C$_6$H$_4$ |
| 148. | 4-(i-C$_3$H$_7$O)—C$_6$H$_4$ |
| 149. | 4-(n-C$_4$H$_9$O)—C$_6$H$_4$ |
| 150. | 3-(t-C$_4$H$_9$O)—C$_6$H$_4$ |
| 151. | 4-(t-C$_4$H$_9$O)—C$_6$H$_4$ |
| 152. | 2-Allyl-O—C$_6$H$_4$ |
| 153. | 3-Allyl-O—C$_6$H$_4$ |
| 154. | 4-Allyl-O—C$_6$H$_4$ |
| 155. | 2-CF$_3$—C$_6$H$_4$ |
| 156. | 3-CF$_3$—C$_6$H$_4$ |
| 157. | 4-CF$_3$—C$_6$H$_4$ |
| 158. | 2-Acetyl-C$_6$H$_4$ |
| 159. | 3-Acetyl-C$_6$H$_4$ |
| 160. | 4-Acetyl-C$_6$H$_4$ |
| 161. | 2-Methoxycarbonyl-C$_6$H$_4$ |
| 162. | 3-Methoxycarbonyl-C$_6$H$_4$ |
| 163. | 4-Methoxycarbonyl-C$_6$H$_4$ |
| 164. | 2-Aminocarbonyl-C$_6$H$_4$ |
| 165. | 3-Aminocarbonyl-C$_6$H$_4$ |
| 166. | 4-Aminocarbonyl-C$_6$H$_4$ |
| 167. | 2-Dimethylaminocarbonyl-C$_6$H$_4$ |
| 168. | 3-Dimethylaminocarbonyl-C$_6$H$_4$ |
| 169. | 4-Dimethylaminocarbonyl-C$_6$H$_4$ |
| 170. | 2-(N-Methylaminocarbonyl)-C$_6$H$_4$ |
| 171. | 3-(N-Methylaminocarbonyl)-C$_6$H$_4$ |
| 172. | 4-(N-Methylaminocarbonyl)-C$_6$H$_4$ |
| 173. | 2-CH$_3$S—C$_6$H$_4$ |
| 174. | 3-CH$_3$S—C$_6$H$_4$ |
| 175. | 4-CH$_3$S—C$_6$H$_4$ |
| 176. | 2-CH$_3$SO$_2$—C$_6$H$_4$ |
| 177. | 3-CH$_3$SO$_2$—C$_6$H$_4$ |
| 178. | 4-CH$_3$SO$_2$—C$_6$H$_4$ |
| 179. | 2-CF$_3$O—C$_6$H$_4$ |
| 180. | 3-CF$_3$O—C$_6$H$_4$ |
| 181. | 4-CF$_3$O—C$_6$H$_4$ |
| 182. | 2-CHF$_2$O—C$_6$H$_4$ |
| 183. | 3-CHF$_2$O—C$_6$H$_4$ |
| 184. | 4-CHF$_2$O—C$_6$H$_4$ |
| 185. | 3-CF$_3$,4-CF$_3$O—C$_6$H$_3$ |
| 186. | 2-CH$_3$NH—C$_6$H$_4$ |
| 187. | 3-CH$_3$NH—C$_6$H$_4$ |
| 188. | 4-CH$_3$NH—C$_6$H$_4$ |
| 189. | 2-(CH$_3$)$_2$N—C$_6$H$_4$ |
| 190. | 3-(CH$_3$)$_2$N—C$_6$H$_4$ |
| 191. | 4-(CH$_3$)$_2$N—C$_6$H$_4$ |
| 192. | 2-Ethoxycarbonyl-C$_6$H$_4$ |
| 193. | 3-Ethoxycarbonyl-C$_6$H$_4$ |
| 194. | 4-Ethoxycarbonyl-C$_6$H$_4$ |
| 195. | 2-CH$_2$FCH$_2$—C$_6$H$_4$ |
| 196. | 3-CH$_2$FCH$_2$—C$_6$H$_4$ |
| 197. | 4-CH$_2$FCH$_2$—C$_6$H$_4$ |
| 198. | 2-CF$_3$CH$_2$—C$_6$H$_4$ |

TABLE A-continued

| No. | R₃ |
|---|---|
| 199. | 3-CF₃CH₂—C₆H₄ |
| 200. | 4-CF₃CH₂—C₆H₄ |
| 201. | 2-CHF₂CF₂—C₆H₄ |
| 202. | 3-CHF₂CF₂—C₆H₄ |
| 203. | 4-CHF₂CF₂—C₆H₄ |
| 204. | 2-CHF₂—C₆H₄ |
| 205. | 3-CHF₂—C₆H₄ |
| 206. | 4-CHF₂—C₆H₄ |
| 207. | 2-NO₂—C₆H₄ |
| 208. | 3-NO₂—C₆H₄ |
| 209. | 4-NO₂—C₆H₄ |
| 210. | 2-CH₃—C₆H₄ |
| 211. | 3-CH₃—C₆H₄ |
| 212. | 4-CH₃—C₆H₄ |
| 213. | 2,3-(CH₃)₂—C₆H₃ |
| 214. | 2,4-(CH₃)₂—C₆H₃ |
| 215. | 2,5-(CH₃)₂—C₆H₃ |
| 216. | 2,6-(CH₃)₂—C₆H₃ |
| 217. | 3,4-(CH₃)₂—C₆H₃ |
| 218. | 3,5-(CH₃)₂—C₆H₃ |
| 219. | 2-C₂H₅—C₆H₄ |
| 220. | 3-C₂H₅—C₆H₄ |
| 221. | 4-C₂H₅—C₆H₄ |
| 222. | 2-i-C₃H₇—C₆H₄ |
| 223. | 3-i-C₃H₇—C₆H₄ |
| 224. | 4-i-C₃H₇—C₆H₄ |
| 225. | 3-tert.-C₄H₉—C₆H₄ |
| 226. | 4-tert.-C₄H₉—C₆H₄ |
| 227. | 2-Vinyl-C₆H₄ |
| 228. | 3-Vinyl-C₆H₄ |
| 229. | 4-Vinyl-C₆H₄ |
| 230. | 2-Allyl-C₆H₄ |
| 231. | 3-Allyl-C₆H₄ |
| 232. | 4-Allyl-C₆H₄ |
| 233. | 2-Propargyl-C₆H₄ |
| 234. | 2-Ethinyl-C₆H₄ |
| 235. | 3-Propargyloxy-C₆H₄ |
| 236. | 4-Butinyloxy-C₆H₄ |
| 237. | 2-C₆H₅—C₆H₄ |
| 238. | 3-C₆H₅—C₆H₄ |
| 239. | 4-C₆H₅—C₆H₄ |
| 240. | 3-CH₃-5-t-C₄H₉—C₆H₃ |
| 241. | 2-F-4-CH₃—C₆H₃ |
| 242. | 2-F-5-CH₃—C₆H₃ |
| 243. | 2-CH₃-4-F—C₆H₃ |
| 244. | 2-CH₃-5-F—C₆H₃ |
| 245. | 2-CH₃-4-Cl—C₆H₃ |
| 246. | 2-F-4-CH₃-O—C₆H₃ |
| 247. | 2-F-4-CH₃CH₂O—C₆H₃ |
| 248. | 2-F-4-i-C₃H₇—C₆H₃ |
| 249. | 4-(4-Chlorophenoxy)phenyl |
| 250. | 4-(4-Trifluoromethylphenoxy)phenyl |
| 251. | 4-(3-Chlorophenoxy)phenyl |
| 252. | 4-(3-Trifluoromethylphenoxy)phenyl |
| 253. | 2-Pyridyl |
| 254. | 3-Pyridyl |
| 255. | 4-Pyridyl |
| 256. | 5-CH₃-Pyridin-2-yl |
| 257. | 5-Cl-Pyridin-2-yl |
| 258. | 6-Cl-Pyridin-2-yl |
| 259. | 3,5-Cl₂-Pyridin-2-yl |
| 260. | 6-CH₃O-Pyridin-2-yl |
| 261. | 6-CH₃-Pyridin-2-yl |
| 262. | 6-Cl-Pyridin-3-yl |
| 263. | 6-CH₃-Pyridin-3-yl |
| 264. | 6-CH₃O-Pyridin-3-yl |
| 265. | 2-Pyrimidinyl |
| 266. | 4-CH₃O-Pyrimidin-2-yl |
| 267. | 4-C₂H₅O-Pyrimidin-2-yl |
| 268. | 4-Cl-Pyrimidin-2-yl |
| 269. | 4-CH₃-Pyrimidin-2-yl |
| 270. | 5-CH₃-Pyrimidin-2-yl |
| 271. | 5-Cl-Pyrimidin-2-yl |
| 272. | 5-CH₃O-Pyrimidin-2-yl |
| 273. | 5-C₂H₅O-Pyrimidin-2-yl |
| 274. | 4-Pyrimidinyl |
| 275. | 2-Cl-Pyrimidin-4-yl |
| 276. | 2-CH₃O-Pyrimidin-4-yl |
| 277. | 2-CH₃-Pyrimidin-4-yl |
| 278. | 6-Cl-Pyrimidin-4-yl |
| 279. | 6-CH₃-Pyrimidin-4-yl |
| 280. | 6-CH₃O-Pyrimidin-4-yl |
| 281. | 5-Pyrimidinyl |
| 282. | 2-CH₃-Pyrimidin-5-yl |
| 283. | 2-Cl-Pyrimidin-5-yl |
| 284. | 2-CH₃O-Pyrimidin-5-yl |
| 285. | 2-C₂H₅O-Pyrimidin-5-yl |
| 286. | 2-Furyl |
| 287. | 4-C₂H₅-Fur-2-yl |
| 288. | 4-CH₃-Fur-2-yl |
| 289. | 4-Cl-Fur-2-yl |
| 290. | 4-CN-Fur-2-yl |
| 291. | 5-CH₃-Fur-2-yl |
| 292. | 5-Cl-Fur-2-yl |
| 293. | 5-CN-Fur-2-yl |
| 294. | 3-Furyl |
| 295. | 5-CH₃-Fur-3-yl |
| 296. | 5-Cl-Fur-3-yl |
| 297. | 5-CN-Fur-3-yl |
| 298. | 2-Thienyl |
| 299. | 4-CH₃-Thien-2-yl |
| 300. | 4-Cl-Thien-2-yl |
| 301. | 4-CN-Thien-2-yl |
| 302. | 5-CH₃-Thien-2-yl |
| 303. | 5-Cl-Thien-2-yl |
| 304. | 5-CN-Thien-2-yl |
| 305. | 3-Thienyl |
| 306. | 5-CH₃-Thien-3-yl |
| 307. | 5-Cl-Thien-3-yl |
| 308. | 5-CN-Thien-3-yl |
| 309. | 1-Methylpropyl-2-yl |
| 310. | 1-Methylpropyl-3-yl |
| 311. | 2-Oxazolyl |
| 312. | 4-CH₃-Oxazol-2-yl |
| 313. | 4-Cl-Oxazol-2-yl |
| 314. | 4-CN-Oxazol-2-yl |
| 315. | 5-CH₃-Oxazol-2-yl |
| 316. | 5-Cl-Oxazol-2-yl |
| 317. | 5-CN-Oxazol-2-yl |
| 318. | 4-Oxazolyl |
| 319. | 2-CH₃-Oxazol-4-yl |
| 320. | 2-Cl-Oxazol-4-yl |
| 321. | 2-CN-Oxazol-4-yl |
| 322. | 5-Oxazolyl |
| 323. | 2-CH₃-Oxazol-5-yl |
| 324. | 2-Cl-Oxazol-5-yl |
| 325. | 2-CN-Oxazol-5-yl |
| 326. | 3-Isoxazolyl |
| 327. | 5-CH₃-Isoxazol-3-yl |
| 328. | 5-Cl-Isoxazol-3-yl |
| 329. | 5-CN-Isoxazol-3-yl |
| 330. | 5-Isoxazolyl |
| 331. | 3-CH₃-Isoxazol-5-yl |
| 332. | 3-Cl-Isoxazol-5-yl |
| 333. | 3-CN-Isoxazol-5-yl |
| 334. | 2-Thiazolyl |
| 335. | 4-CH₃-Thiazol-2-yl |
| 336. | 4-Cl-Thiazol-2-yl |
| 337. | 4-CN-Thiazol-2-yl |
| 338. | 5-CH₃-Thiazol-2-yl |
| 339. | 5-Cl-Thiazol-2-yl |
| 340. | 5-CN-Thiazol-2-yl |
| 341. | 4-Thiazolyl |
| 342. | 2-CH₃-Thiazol-4-yl |
| 343. | 2-Cl-Thiazol-4-yl |
| 344. | 2-CN-Thiazol-4-yl |
| 345. | 2-CH₃S-Thiazol-4-yl |
| 346. | 5-Thiazolyl |
| 347. | 2-CH₃-Thiazol-5-yl |
| 348. | 2-Cl-Thiazol-5-yl |
| 349. | 2-CN-Thiazol-5-yl |
| 350. | 3-Isothiazolyl |
| 351. | 5-CH₃-Isothiazol-3-yl |
| 352. | 5-Cl-Isothiazol-3-yl |

TABLE A-continued

| No. | R₃ |
|---|---|
| 353. | 5-CN-Isothiazol-3-yl |
| 354. | 5-Isothiazolyl |
| 355. | 3-CH₃-Isothiazol-5-yl |
| 356. | 3-Cl-Isothiazol-5-yl |
| 357. | 3-CN-Isothiazol-5-yl |
| 358. | 2-Imidazolyl |
| 359. | 4-CH₃-Imidazol-2-yl |
| 360. | 4-Cl-Imidazol-2-yl |
| 361. | 4-CN-Imidazol-2-yl |
| 362. | 1-CH₃-Imidazol-2-yl |
| 363. | 1-CH₃-4-Cl-Imidazol-2-yl |
| 364. | 1,4-(CH₃)₂-Imidazol-2-yl |
| 365. | 1-CH₃-5-Cl-Imidazol-2-yl |
| 366. | 1,5-(CH₃)₂-Imidazol-2-yl |
| 367. | 4-Imidazolyl |
| 368. | 2-CH₃-Imidazol-4-yl |
| 369. | 2-Cl-Imidazol-4-yl |
| 370. | 1-CH₃-Imidazol-4-yl |
| 371. | 1,2-(CH₃)₂-Imidazol-4-yl |
| 372. | 1-CH₃-2-Cl-Imidazol-4-yl |
| 373. | 1-CH₃-Imidazol-5-yl |
| 374. | 1-CH₃-3-Cl-Imidazol-5-yl |
| 375. | 1,2-(CH₃)₂-Imidazol-5-yl |
| 376. | 3-Pyrazolyl |
| 377. | 5-CH₃-Pyrazol-3-yl |
| 378. | 5-Cl-Pyrazol-3-yl |
| 379. | 5-CN-Pyrazol-3-yl |
| 380. | 1-CH₃-Pyrazol-3-yl |
| 381. | 1-CH₃-4-Cl-Pyrazol-3-yl |
| 382. | 1-CH₃-5-Cl-Pyrazol-3-yl |
| 383. | 1,5-(CH₃)₂-Pyrazol-3-yl |
| 384. | 1-CH₃-Pyrazol-5-yl |
| 385. | 1-CH₃-3-Cl-Pyrazol-5-yl |
| 386. | 1,3-(CH₃)₂-Pyrazol-5-yl |
| 387. | 4-Pyrazolyl |
| 388. | 3-Cl-Pyrazol-4-yl |
| 389. | 3-CH₃-Pyrazol-4-yl |
| 390. | 1-CH₃-Pyrazol-4-yl |
| 391. | 1-CH₃-3-Cl-Pyrazol-4-yl |
| 392. | 1,3-(CH₃)₂-Pyrazol-4-yl |
| 393. | 1,3,4-Oxadiazol-5-yl |
| 394. | 2-CH₃-1,3,4-Oxadiazol-5-yl |
| 395. | 2-Cl-1,3,4-Oxadiazol-5-yl |
| 396. | 2-CF₃-1,3,4-Oxadiazol-5-yl |
| 397. | 2-i-C₃H₇-1,3,4-Oxadiazol-5-yl |
| 398. | 2-CH₃O-1,3,4-Oxadiazol-5-yl |
| 399. | 1,2,4-Oxadiazol-3-yl |
| 400. | 5-CH₃-1,2,4-Oxadiazol-3-yl |
| 401. | 5-i-C₃H₇-1,2,4-Oxadiazol-3-yl |
| 402. | 5-Cl-1,2,4-Oxadiazol-3-yl |
| 403. | 5-CF₃-1,2,4-Oxadiazol-3-yl |
| 404. | 1,2,4-Triazol-3-yl |
| 405. | 1-CH₃-1,2,4-Triazol-3-yl |
| 406. | 1-Pyrrolyl |
| 407. | 3-CH₃-Pyrrol-1-yl |
| 408. | 1-Pyrazolyl |
| 409. | 3-CH₃-Pyrazol-1-yl |
| 410. | 3-CF₃-Pyrazol-1-yl |
| 411. | 4-CH₃-Pyrazol-1-yl |
| 412. | 4-Cl-Pyrazol-1-yl |
| 413. | 4-Ethoxycarbonyl-Pyrazol-1-yl |
| 414. | 3-CH₃-4-Br-Pyrazol-1-yl |
| 415. | 1-Imidazolyl |
| 416. | 4-CH₃-Imidazol-1-yl |
| 417. | 4,5-Cl₂-Imidazol-1-yl |
| 418. | 2,4-(CH₃)₂-Imidazol-1-yl |
| 419. | 1,2,4-Triazol-1-yl |
| 420. | 1,3,4-Triazol-1-yl |
| 421. | 3,5-(CH₃)₂-1,2,4-Triazol-1-yl |
| 422. | 1-Piperidinyl |
| 423. | 1-Pyrrolidinyl |
| 424. | 1-Morpholinyl |
| 425. | 2-Δ²-Thiazolinyl |
| 426. | 5-CH₃-Δ²-Thiazolin-2-yl |
| 427. | 5,5-(CH₃)₂-Δ²-Thiazolin-2-yl |
| 428. | 4,5-(CH₃)₂-Δ²-Thiazolin-2-yl |
| 429. | 2-Δ²-Oxazolinyl |
| 430. | 4-CH₃-Δ²-Oxazolin-2-yl |
| 431. | 4,4-(CH₃)₂-Δ²-Oxazolin-2-yl |
| 432. |  |
| 433. |  |
| 434. |  |
| 435. | Cyclopropoxy |
| 436. | Cyclobutoxy |
| 437. | Cyclopentoxy |
| 438. | Cyclohexyloxy |
| 439. | Phenoxy |
| 440. | 1-Naphthyloxy |
| 441. | 2-Naphthyloxy |
| 442. | 2-F-C₆H₄O |
| 443. | 3-F-C₆H₄O |
| 444. | 4-F-C₆H₄O |
| 445. | 2,3-F₂—C₆H₃O |
| 446. | 2,4-F₂—C₆H₃O |
| 447. | 2,5-F₂—C₆H₃O |
| 448. | 2,6-F₂—C₆H₃O |
| 449. | 3,4-F₂—C₆H₃O |
| 450. | 3,5-F₂—C₆H₃O |
| 451. | 2-Cl—C₆H₄O |
| 452. | 3-Cl—C₆H₄O |
| 453. | 4-Cl—C₆H₄O |
| 454. | 2,3-Cl₂—C₆H₃O |
| 455. | 2,4-Cl₂—C₆H₃O |
| 456. | 2,5-Cl₂—C₆H₃O |
| 457. | 2,6-Cl₂—C₆H₃O |
| 458. | 3,4-Cl₂—C₆H₃O |
| 459. | 3,5-Cl₂—C₆H₃O |
| 460. | 2,3,4-Cl₃—C₆H₂O |
| 461. | 2,3,5-Cl₃—C₆H₂O |
| 462. | 2,3,6-Cl₃—C₆H₂O |
| 463. | 2,4,5-Cl₃—C₆H₂O |
| 464. | 2,4,6-Cl₃—C₆H₂O |
| 465. | 3,4,5-Cl₃—C₆H₂O |
| 466. | 2-Br—C₆H₄O |
| 467. | 3-Br—C₆H₄O |
| 468. | 4-Br—C₆H₄O |
| 469. | 2,3-Br₂—C₆H₃O |
| 470. | 2,4-Br₂—C₆H₃O |
| 471. | 2,5-Br₂—C₆H₃O |
| 472. | 2,6-Br₂—C₆H₃O |
| 473. | 3,4-Br₂—C₆H₃O |
| 474. | 3,5-Br₂—C₆H₃O |
| 475. | 2-F-3-Cl—C₆H₃O |
| 476. | 2-F-4-Cl—C₆H₃O |
| 477. | 2-F-5-Cl—C₆H₃O |
| 478. | 2-F-3-Br—C₆H₃O |
| 479. | 2-F-4-Br—C₆H₃O |
| 480. | 2-F-5-Br—C₆H₃O |
| 481. | 2-Cl-3-Br—C₆H₃O |
| 482. | 2-Cl-4-Br—C₆H₃O |
| 483. | 2-Cl-5-Br—C₆H₃O |
| 484. | 3-F-4-Cl—C₆H₃O |
| 485. | 3-F-5-Cl—C₆H₃O |
| 486. | 3-F-6-Cl—C₆H₃O |
| 487. | 3-F-4-Br—C₆H₃O |

TABLE A-continued

| No. | R₃ |
|---|---|
| 488. | 3-F-5-Br—C$_6$H$_3$O |
| 489. | 3-F-6-Br—C$_6$H$_3$O |
| 490. | 3-Cl-4-Br—C$_6$H$_3$O |
| 491. | 3-Cl-5-Br—C$_6$H$_3$O |
| 492. | 3-Cl-6-Br—C$_6$H$_3$O |
| 493. | 4-F-5-Cl—C$_6$H$_3$O |
| 494. | 4-F-6-Cl—C$_6$H$_3$O |
| 495. | 4-F-5-Br—C$_6$H$_3$O |
| 496. | 4-F-6-Br—C$_6$H$_3$O |
| 497. | 4-Cl-5-Br—C$_6$H$_3$O |
| 498. | 5-F-6-Cl—C$_6$H$_3$O |
| 499. | 5-F-6-Br—C$_6$H$_3$O |
| 500. | 5-Cl-6-Br—C$_6$H$_3$O |
| 501. | 3-Br-4-Cl-5-Br—C$_6$H$_2$O |
| 502. | 2-CN—C$_6$H$_4$O |
| 503. | 3-CN—C$_6$H$_4$O |
| 504. | 4-CN—C$_6$H$_4$O |
| 505. | 4-Dimethylaminocarbonyl-C$_6$H$_4$O |
| 506. | 2-(N-Methylaminocarbonyl)-C$_6$H$_4$O |
| 507. | 3-(N-Methylaminocarbonyl)-C$_6$H$_4$O |
| 508. | 4-(N-Methylaminocarbonyl)-C$_6$H$_4$O |
| 509. | 2-CH$_3$S—C$_6$H$_4$O |
| 510. | 3-CH$_3$S—C$_6$H$_4$O |
| 511. | 4-CH$_3$S—C$_6$H$_4$O |
| 512. | 2-CH$_3$SO$_2$—C$_6$H$_4$O |
| 513. | 3-CH$_3$SO$_2$—C$_6$H$_4$O |
| 514. | 4-CH$_3$SO$_2$—C$_6$H$_4$O |
| 515. | 2-CF$_3$O—C$_6$H$_4$O |
| 516. | 3-CF$_3$O—C$_6$H$_4$O |
| 517. | 4-CF$_3$O—C$_6$H$_4$O |
| 518. | 2-CHF$_2$O—C$_6$H$_4$O |
| 519. | 4-CHF$_2$O—C$_6$H$_4$O |
| 520. | 4-CHF$_2$O—C$_6$H$_4$O |
| 521. | 3-CF$_3$-4-CF$_3$O—C$_6$H$_3$O |
| 522. | 2-CH$_3$NH—C$_6$H$_4$O |
| 523. | 3-CH$_3$NH—C$_6$H$_4$O |
| 524. | 4-CH$_3$NH—C$_6$H$_4$O |
| 525. | 2-(CH$_3$)$_2$N—C$_6$H$_4$O |
| 526. | 3-(CH$_3$)$_2$N—C$_6$H$_4$O |
| 527. | 4-(CH$_3$)$_2$N—C$_6$H$_4$O |
| 528. | 2-Ethoxycarbonyl-C$_6$H$_4$O |
| 529. | 3-Ethoxycarbonyl-C$_6$H$_4$O |
| 530. | 4-Ethoxycarbonyl-C$_6$H$_4$O |
| 531. | 2-CH$_2$FCH$_2$—C$_6$H$_4$O |
| 532. | 3-CH$_2$FCH$_2$—C$_6$H$_4$O |
| 533. | 4-CH$_2$FCH$_2$—C$_6$H$_4$O |
| 534. | 2-CF$_3$CH$_2$—C$_6$H$_4$O |
| 535. | 3-CF$_3$CH$_2$—C$_6$H$_4$O |
| 536. | 4-CF$_3$CH$_2$—C$_6$H$_4$O |
| 537. | 2-CHF$_2$CF$_2$—C$_6$H$_4$O |
| 538. | 3-CHF$_2$CF$_2$—C$_6$H$_4$O |
| 539. | 4-CHF$_2$CF$_2$—C$_6$H$_4$O |
| 540. | 2-CHF$_2$—C$_6$H$_4$O |
| 541. | 3-CHF$_2$—C$_6$H$_4$O |
| 542. | 4-CHF$_2$—C$_6$H$_4$O |
| 543. | 2-CH$_3$O—C$_6$H$_4$O |
| 544. | 3-CH$_3$O—C$_6$H$_4$O |
| 545. | 4-CH$_3$O—C$_6$H$_4$O |
| 546. | 2,3-(CH$_3$O)$_2$—C$_6$H$_3$O |
| 547. | 2,4-(CH$_3$O)$_2$—C$_6$H$_3$O |
| 548. | 2,5-(CH$_3$O)$_2$—C$_6$H$_3$O |
| 549. | 3,4-(CH$_3$O)$_2$—C$_6$H$_3$O |
| 550. | 3,5-(CH$_3$O)$_2$—C$_6$H$_3$O |
| 551. | 3,4,5-(CH$_3$O)$_3$—C$_6$H$_2$O |
| 552. | 2-C$_2$H$_5$O—C$_6$H$_4$O |
| 553. | 3-C$_2$H$_5$O—C$_6$H$_4$O |
| 554. | 4-C$_2$H$_5$O—C$_6$H$_4$O |
| 555. | 2-(n-C$_3$H$_7$O)—C$_6$H$_4$O |
| 556. | 3-(n-C$_3$H$_7$O)—C$_6$H$_4$O |
| 557. | 4-(n-C$_3$H$_7$O)—C$_6$H$_4$O |
| 558. | 2-(i-C$_3$H$_7$O)—C$_6$H$_4$O |
| 559. | 3-(i-C$_3$H$_7$O)—C$_6$H$_4$O |
| 560. | 4-(i-C$_3$H$_7$O)—C$_6$H$_4$O |
| 561. | 4-(n-C$_4$H$_9$O)—C$_6$H$_4$O |
| 562. | 3-(t-C$_4$H$_9$O)—C$_6$H$_4$O |
| 563. | 4-(t-C$_4$H$_9$O)—C$_6$H$_4$O |
| 564. | 2-Allyl-O—C$_6$H$_4$O |
| 565. | 3-Allyl-O—C$_6$H$_4$O |
| 566. | 4-Allyl-O—C$_6$H$_4$O |
| 567. | 2-CF$_3$—C$_6$H$_4$O |
| 568. | 3-CF$_3$—C$_6$H$_4$O |
| 569. | 4-CF$_3$—C$_6$H$_4$O |
| 570. | 2-Acetyl-C$_6$H$_4$O |
| 571. | 3-Acetyl-C$_6$H$_4$O |
| 572. | 4-Acetyl-C$_6$H$_4$O |
| 573. | 2-Methoxycarbonyl-C$_6$H$_4$O |
| 574. | 3-Methoxycarbonyl-C$_6$H$_4$O |
| 575. | 4-Methoxycarbonyl-C$_6$H$_4$O |
| 576. | 2-Aminocarbonyl-C$_6$H$_4$O |
| 577. | 3-Aminocarbonyl-C$_6$H$_4$O |
| 578. | 4-Aminocarbonyl-C$_6$H$_4$O |
| 579. | 2-Dimethylaminocarbonyl-C$_6$H$_4$O |
| 580. | 3-Dimethylaminocarbonyl-C$_6$H$_4$O |
| 581. | 2-NO$_2$—C$_6$H$_4$O |
| 582. | 3-NO$_2$—C$_6$H$_4$O |
| 583. | 4-NO$_2$—C$_6$H$_4$O |
| 584. | 2-CH$_3$—C$_6$H$_4$O |
| 585. | 3-CH$_3$—C$_6$H$_4$O |
| 586. | 4-CH$_3$—C$_6$H$_4$O |
| 587. | 2,3-(CH$_3$)$_2$—C$_6$H$_3$O |
| 588. | 2,4-(CH$_3$)$_2$—C$_6$H$_3$O |
| 589. | 2,5-(CH$_3$)$_2$—C$_6$H$_3$O |
| 590. | 2,6-(CH$_3$)$_2$—C$_6$H$_3$O |
| 591. | 3,4-(CH$_3$)$_2$—C$_6$H$_3$O |
| 592. | 3,5-(CH$_3$)$_2$—C$_6$H$_3$O |
| 593. | 2-C$_2$H$_5$—C$_6$H$_4$O |
| 594. | 3-C$_2$H$_5$—C$_6$H$_4$O |
| 595. | 4-C$_2$H$_5$—C$_6$H$_4$O |
| 596. | 2-i-C$_3$H$_7$—C$_6$H$_4$O |
| 597. | 3-i-C$_3$H$_7$—C$_6$H$_4$O |
| 598. | 4-i-C$_3$H$_7$—C$_6$H$_4$O |
| 599. | 3-tert.-C$_4$H$_9$—C$_6$H$_4$O |
| 600. | 4-tert.-C$_4$H$_9$—C$_6$H$_4$O |
| 601. | 2-Vinyl-C$_6$H$_4$O |
| 602. | 3-Vinyl-C$_6$H$_4$O |
| 603. | 4-Vinyl-C$_6$H$_4$O |
| 604. | 2-Allyl-C$_6$H$_4$O |
| 605. | 3-Allyl-C$_6$H$_4$O |
| 606. | 4-Allyl-C$_6$H$_4$O |
| 607. | 2-C$_6$H$_5$—C$_6$H$_4$O |
| 608. | 3-C$_6$H$_5$—C$_6$H$_4$O |
| 609. | 4-C$_6$H$_5$—C$_6$H$_4$O |
| 610. | 3-CH$_3$-5-t-C$_4$H$_9$—C$_6$H$_3$O |
| 611. | 2-F-4-CH$_3$—C$_6$H$_3$O |
| 612. | 2-F-5-CH$_3$—C$_6$H$_3$O |
| 613. | 2-CH$_3$-4-F—C$_6$H$_3$O |
| 614. | 2-CH$_3$-5-F—C$_6$H$_3$O |
| 615. | 2-CH$_3$-4-Cl—C$_6$H$_3$O |
| 616. | 2-Pyridyloxy |
| 617. | 3-Pyridyloxy |
| 618. | 4-Pyridyloxy |
| 619. | 2-Pyrimidinyloxy |
| 620. | 4-Pyrimidinyloxy |
| 621. | 5-Pyrimidinyloxy |
| 622. | 1-CH$_3$-Piperidinyl-3-oxy |
| 623. | 1-CH$_3$-Piperidinyl-4-oxy |

TABLE 37

Compounds of formula

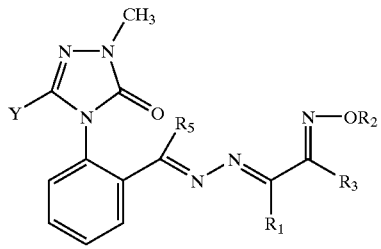

| No. | Y | $R_1$ | $R_2$ | $R_5$ | $R_3$ | phys. data m.p. |
|---|---|---|---|---|---|---|
| 37.1. | $OCH_3$ | $CH_3$ | $CH_3$ | H | $CH_3$ | 146–148° C. |
| 37.2. | $OCH_3$ | $CH_3$ | $CH_3$ | H | 4-$CH_3$—$C_6H_4$ | 154–155° C. |
| 37.3. | $OCH_3$ | $CH_3$ | $CH_3$ | H | 4-$CH_3CH_2$—$C_6H_4$ | 96–98° C. |
| 37.4. | $OCH_3$ | $CH_3$ | $CH_3$ | H | 4-F—$C_6H_4$ | 190–193° C. |
| 37.5. | $OCH_3$ | $CH_3$ | $CH_3$ | H | 4-Cl—$C_6H_4$ | 158–159° C. |
| 37.6. | $OCH_3$ | $CH_3$ | $CH_3$ | H | 4-Br—$C_6H_4$ | 151–153° C. |
| 37.7. | $OCH_3$ | $CH_3$ | $CH_3$ | H | 4-$CH_3O$—$C_6H_4$ | 146° C. |
| 37.8. | $OCH_3$ | $CH_3$ | $CH_3$ | H | 3-$CF_3$—$C_6H_4$ | 157–161° C. |
| 37.9. | $OCH_3$ | $CH_3$ | $CH_3$ | H | 4-$CH_3CH_2O$—$C_6H_4$ | 146–148° C. |
| 37.10. | $OCH_3$ | $CH_3$ | $CH_3$ | H | 2,4-$F_2$—$C_6H_3$ | |
| 37.11. | $OCH_3$ | $CH_3$ | $CH_3$ | $CH_3$ | 4-F—$C_6H_4$ | 162–163° C. |
| 37.12. | $OCH_3$ | $CH_3$ | $CH_3$ | $CH_3$ | 4-Cl—$C_6H_4$ | 152–154° C. |

TABLE 38

Intermediates of formula II

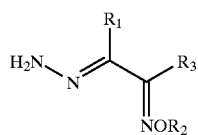

| No. | $R_1$ | $R_2$ | $R_3$ | phys. data |
|---|---|---|---|---|
| 38.1. | $CH_3$ | $CH_3$ | 4-$CH_3$—$C_6H_4$ | 112–114° |
| 38.2. | $CH_3$ | $CH_3$ | 4-$CH_3CH_2$—$C_6H_4$ | 92–95° |
| 38.3. | $CH_3$ | $CH_3$ | 4-F—$C_6H_4$ | 134–136° |
| 38.4. | $CH_3$ | $CH_3$ | 4-Cl—$C_6H_4$ | 118–119° |
| 38.5. | $CH_3$ | $CH_3$ | 4-Br—$C_6H_4$ | 127–129° |
| 38.6. | $CH_3$ | $CH_3$ | 4-$CH_3O$—$C_6H_4$ | 87–90° |
| 38.7. | $CH_3$ | $CH_3$ | 4-$CH_3CH_2O$—$C_6H_4$ | 92–94° |
| 38.8. | $CH_3$ | $CH_3$ | 3-$CF_3$—$C_6H_4$ | 96–98° |
| 38.9. | $CH_3$ | $CH_3$ | $CH_3$ | 94–97° |

Formulations may be prepared analogously to those described for example in WO 97/33890.

BIOLOGICAL EXAMPLES

In the following patho-systems, compounds from the tables display good activity:

EXAMPLE B-1

Activity against *Puccinia graminis* on Wheat a) Residual Protective Action 6 days after planting, wheat plants are sprayed to drip point with an aqueous spray mixture prepared from a wettable powder of the active ingredient (0.02% active substance), and 24 hours later they are infected with a uredospore suspension of the fungus. After an incubation period of 48 hours (conditions: 95 to 100 percent relative humidity at 20°), the plants are placed in a greenhouse at 22°. 12 days after infection, the fungal attack is evaluated.

b) Systemic Action 5 days after planting, an aqueous spray mixture prepared from a wettable powder of the active ingredient (0.006% active substance, based on soil volume) is poured onto wheat plants. Care is taken that the spray mixture does not come into contact with the parts of the plants that are above ground. 48 hours later, the plants are infected with a uredospore suspension of the fungus. After an incubation period of 48 hours (conditions: 95 to 100 percent relative humidity at 20°), the plants are placed in a greenhouse at 22°. 12 days after infection, the fungal attack is evaluated.

EXAMPLE B-2

Activity against *Phytophthora infestans* on Tomatoes a) Residual Protective Action After cultivating for three weeks, tomato plants are sprayed to drip point with an aqueous spray mixture prepared from a wettable powder of the active ingredient (0.02% active substance), and 24 hours later they are infected with a sporangia suspension of the fungus. Evaluation of the fungal attack takes place 5 days after infection, during which time conditions of 90 to 100 percent relative humidity and a temperature of 20° are maintained.

b) Systemic Action

After cultivating for three weeks, an aqueous spray mixture prepared from a wettable powder of the active ingredient (0.006% active substance, based on soil volume) is poured onto tomato plants. Care is taken that the spray mixture does not come into contact with the parts of the plants that are above ground. 48 hours later, the plants are infected with a sporangia suspension of the fungus. Evaluation of the fungal attack takes place 5 days after infection, during which time conditions of 90 to 100 percent relative humidity and a temperature of 20° are maintained.

EXAMPLE B-3

Residual Protective Action against *Cercospora arachidicola* on Peanuts

Peanut plants of 10 to 15 cm height are sprayed to drip point with an aqueous spray mixture prepared from a wettable powder of the active ingredient (0.02% active substance), and 48 hours later they are infected with a conidia suspension of the fungus. The plants are incubated for 72 hours at 21° and at high humidity, and then placed in a greenhouse until the typical leaf spots appear. Evaluation of the activity of the active substance is made 12 days after infection and is based on the number and size of leaf spots.

EXAMPLE B-4

Activity against *Plasmopara viticola* on Grapevines

Vine seedlings at the 4 to 5 leaf stage are sprayed to drip point with an aqueous spray mixture prepared from a wettable powder of the active ingredient (0.02% active substance), and 24 hours later they are infected with a sporangia suspension of the fungus. Evaluation of the fungal attack takes place 6 days after infection, during which time conditions of 95 to 100 percent relative humidity and a temperature of 20° are maintained.

EXAMPLE B-5

Activity against *Colletotrichum lagenarium* on Cucumbers

After cultivating for 2 weeks, cucumber plants are sprayed with an aqueous spray mixture prepared from a wettable powder of the active ingredient (concentration 0.002%). After 2 days, the plants are infected with a spore suspension ($1.5 \times 10^5$ spores/ml) of the fungus, and incubated for 36 hours at 23° C. and at high humidity. Incubation then continues at normal humidity and at ca. 22° C. The fungal attack that has set in is evaluated 8 days after infection.

EXAMPLE B-6

Residual Protective Action against *Venturia inaequalis* on Apples

Apple cuttings with new shoots of 10 to 20 cm length are sprayed to drip point with an aqueous spray mixture prepared from a wettable powder of the active ingredient (0.02% active substance), and 24 hours later they are infected with a conidia suspension of the fungus. The plants are incubated for 5 days at 90 to 100 percent relative humidity and placed in a greenhouse for a further 10 days at 20 to 24°. 12 days after infection, the fungal attack is evaluated.

EXAMPLE B-7

Activity against *Erysiphe graminis* on Barley
a) Residual Protective Action
Barley plants of approximately 8 cm height are sprayed to drip point with an aqueous spray mixture prepared from a wettable powder of the active ingredient (0.02% active substance), and 3 to 4 hours later they are dusted with conidia of the fungus. The infected plants are placed in a greenhouse at 22°. 12 days after infection, the fungal attack is evaluated.
b) Systemic Action
An aqueous spray mixture prepared from a wettable powder of the active ingredient (0.002% active substance, based on soil volume) is poured onto barley plants of approximately 8 cm height. Care is taken that the spray mixture does not come into contact with the parts of the plants that are above ground. 48 hours later, the plants are dusted with conidia of the fungus. The infected plants are placed in a greenhouse at 22°. 12 days after infection, the fungal attack is evaluated.

EXAMPLE B-8

Activity against *Podosphaera leucotricha* on Apple Shoots

Apple cuttings with new shoots of ca. 15 cm length are sprayed with a spray mixture (0.06% active substance). After 24 hours, the treated plants are infected with a conidia suspension of the fungus and placed in a plant-growth chamber at 70% relative humidity and at 20° C. 12 days after infection, the fungal attack is evaluated.

BIOLOGICAL EXAMPLES

B. *Insecticidal* Activity

EXAMPLE B-9

Activity against *Aphis craccivora*

Pea seedlings are infected with *Aphis craccivora*, subsequently sprayed with a spray mixture containing 100 ppm of active ingredient, and then incubated at 20°. The percentage reduction of the population (% response) is determined 3 and 6 days later by comparing the total number of dead aphids on the treated plants with those on the untreated plants. Compounds of the tables show good response in this test, i.e. a mortality rate or over 80%.

EXAMPLE B-10

Activity against *Diabrotica balteata*

Maize seedlings are sprayed with an aqueous emulsion spray mixture containing 400 ppm of active ingredient, when the spray coating has dried on they are colonised with 10 larvae of the second stage of *Diabrotica balteata* and then placed in a plastic container. The percentage reduction of the population (% response) is determined 6 days later by comparing the total number of dead larvae on the treated plants with those on the untreated plants.

EXAMPLE B-11

Activity against *Heliothis virescens*

Young soya plants are sprayed with an aqueous emulsion spray mixture containing 100 ppm of active ingredient, when the spray coating has dried on they are colonised with 10 grubs of the first stage of *Heliothis virescens* and then placed in a plastic container. The percentage reduction of the population and of the feeding damage (% response) is determined 6 days later by comparing the total number of dead caterpillars and the feeding damage on the treated plants with those on the untreated plants.

EXAMPLE B-12

Activity against *Spodoptera littoralis*

Young soya plants are sprayed with an aqueous emulsion spray mixture containing 100 ppm of active ingredient, when the spray coating has dried on they are colonised with 10 caterpillars of the third stage of *Spodoptera littoralis* and then placed in a plastic container. The percentage reduction of the population and of the feeding damage (% response) is determined 3 days later by comparing the total number of dead caterpillars and the feeding damage on the treated plants with those on the untreated plants.

B-13

Activity against *Nilaparvata lugens*

Rice plants are sprayed with an aqueous emulsion spray mixture containing 100 ppm of active ingredient. After the spray coating has dried on, the rice plants are colonised with plant and leaf-hopper larvae of the second and third stage. 21 days later they are evaluated. The percentage reduction of the population (% response) is determined by comparing the number of surviving plant and leaf-hoppers on the treated plants with those on the untreated plants.

B-14

Activity against *Plutella xylostella* Caterpillars

Young cabbage plants are sprayed with an aqueous emulsion spray mixture containing 100 ppm of active ingredient. After the spray coating has dried on, the cabbage plants are colonised with 10 grubs of the third stage of *Plutella xylostella* and placed in a plastic container. Three days later they are evaluated. The percentage reduction of the population and percentage reduction in feeding damage (% response) are determined by comparing the total number of dead caterpillars and the extent of feeding damage on the treated plants with those on the untreated plants.

EXAMPLE B-15

Activity against *Musca domestica*

A sugar cube is treated with a solution of the test compound in such a way that the concentration of test compound in the sugar, after drying over night, is 250 ppm. This treated cube is place on an aluminium dish with a wet wad of cottonwool and 10 adult *Musca domestica* of an OP-resistant strain, covered with a beaker and incubated at 25° C. The mortality rate is determined after 24 hours.

BIOLOGICAL EXAMPLES

C. *Acaricidal* Activity

B-16

Activity against *Tetranychus urticae*

Young bean plants are colonised with a mixed population of *Tetranychus urticae* and are sprayed one day later with an aqueous emulsion spray mixture containing 400 ppm of active ingredient. The plants are subsequently incubated for 6 days at 25° C. and then evaluated. The percentage reduction of the population (% response) is determined by comparing the total number of dead eggs, larvae, and adults on the treated plants with those on the untreated plants.

B-17

Activity on Mixed Population of *Tetranychus cinnabarinus* Dilution Series

Bush beans at the 2-leaf stage are colonised with a mixed population (eggs, larvae/nymphs, adults) of an OP-tolerant strain of *Tetranychus cinnabarinus*. 24 hours after infection, the products are applied to the plants in an automatic spray canister at doses of 200, 100, 50 mg AS/I. The substances are ready-formulated and are diluted with water to the appropriate doses. The test is evaluated 2 and 7 days after application by the percentage mortality of eggs, larvae/nymphs and adults.

B-18

Activity against *Boophilus microplus*

Fully engorged female adult ticks are adhered to a PVC sheet, covered with a wad of cottonwool and then 10 ml of aqueous test solution, containing 125 ppm active ingredient, is poured over them. The cottonwool is removed and the ticks are incubated for 4 weeks to lay eggs. The activity is shown either in the case of females as mortality or sterility or in the case of eggs as ovicidal activity.

What is claimed is:

1. A compound of formula I wherein:

Y represents methoxy;

$R_1$ represents methyl;

$R_2$ represents methyl;

$R_3$ represents $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkinyl, $C_2$–$C_6$-alkinyloxy, $C_1$–$C_6$-alkoxycarbonyl or CN, wherein, with the exception of CN, the above-mentioned groups may be substituted by one or more substituents selected from halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylaminocarbonyl, di-$C_1$–$C_6$-alkylaminocarbonyl, $C_2$–$C_6$-alkenyloxy, $C_3$–$C_6$-cycloalkyl, $C_3$–$C_6$-cycloalkoxy, phenyl, naphthyl, phenyoxy, naphthyloxy, wherein the cyclic radical may be substituted by one or more substituents selected from halogen, cyano, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted phenyl, optionally substituted naphthyl, optionally substituted phenyoxy, optionally substituted naphthyloxy or $R_3$ represents phenyl, naphthyl, phenyoxy, naphthyloxy wherein the above-mentioned groups may be substituted by one or more substituents selected from halogen, $C_1$–$C_6$-alkyl, $C_1$–$C_6$-alkoxy, halo-$C_1$–$C_6$-alkoxy, halo-$C_1$–$C_6$-alkyl, $C_1$–$C_6$-alkylthio, halo-$C_1$–$C_6$-alkylthio, $C_1$–$C_6$-alkylsulfinyl, halo-$C_1$–$C_6$-alkylsulfinyl, $C_1$–$C_6$-alkyl-sulfonyl, halo-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkylcarbonyl, halo-$C_1$–$C_6$-alkylcarbonyl, $C_1$–$C_6$- alkoxycarbonyl, halo-$C_1$–$C_6$-alkoxycarbonyl, $C_1$–$C_6$-alkylaminocarbonyl, di-($C_1$–$C_6$-alkyl)-aminocarbonyl, $C_1$–$C_6$-alkylaminothiocarbonyl, di-($C_1$–$C_6$-alkyl)-aminothiocarbonyl, $C_1$–$C_6$-alkylamino, di-($C_1$–$C_6$-alkyl)-amino, $NO_2$, an unsubstituted $C_1$–$C_4$-alkylenedioxy group or one which is mono- to tetra-substituted by $C_1$–$C_4$-alkyl and/or by halogen, or CN, $SF_5$ and $QR_4$; wherein Q represents a direct bond, O, O($C_1$–$C_6$-alkylene), ($C_1$–$C_6$-alkylene)O, S(=O)p, S(=O)p($C_1$–$C_6$-alkylene), ($C_1$–$C_6$-alkylene)S(=O)p, $C_1$–$C_8$-alkylene, $C_2$–$C_6$-alkenylene or $C_2$–$C_6$-alkinylene;

$R_4$ represents an unsubstituted $C_2$–$C_6$-alkenyl- or $C_2$–$C_6$-alkinyl group or one which is substituted by 1 to 3 halogen atoms, a ($C_1$–$C_4$-alkyl)$_3$Si group, CN, an unsubstituted or mono- to penta-substituted $C_3$–$C_6$-cycloalkyl, phenyl, naphthyl, wherein the substituents are selected from halogen, $C_1$–$C_6$-alkyl, halo-$C_1$–$C_6$-alkyl, $C_1$–$C_6$-alkoxy, halo-$C_1$–$C_6$-alkoxy, phenoxy and CN;

p is 0, 1 or 2; and $R_5$ represents hydrogen.

2. A compound of formula I.1,

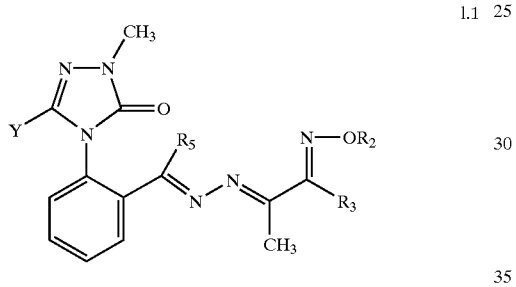

I.1 wherein

Y is methoxy;

$R_2$ is methyl;

$R_3$ is $C_1$–$C_6$-alkyl, $C_1$–$C_6$-alkoxy, $C_1$–$C_6$-alkoxycarbonyl, CN, $C_3$–$C_6$-cycloalkyl, phenyl, naphthyl, phenyoxy, naphthlyoxy wherein with the exception of CN, the above-mentioned groups may be substituted by one or more substituents selected from halogen, $C_1$–$C_6$-alkyl, $C_1$–$C_6$-alkoxy, halo-$C_1$–$C_6$-alkoxy, halo-$C_1$–$C_6$-alkyl, $C_1$–$C_6$-alkylthio, halo-$C_1$–$C_6$-alkylthio, $C_1$–$C_6$-alkylsulfinyl, halo-$C_1$–$C_6$-alkylsulfinyl, $C_1$–$C_6$-alkylsulfonyl, halo-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkylcarbonyl, halo-$C_1$–$C_6$-alkylcarbonyl, $C_1$–$C_6$-alkoxycarbonyl, halo-$C_1$–$C_6$-alkoxycarbonyl, $C_1$–$C_6$-alkylaminocarbonyl, di-($C_1$–$C_6$-alkyl)-aminocarbonyl, $C_1$–$C_6$-alkylaminothiocarbonyl, di-($C_1$–$C_6$-alkyl)-aminothiocarbonyl, $C_1$–$C_6$-alkylamino, di-($C_1$–$C_6$-alkyl)-amino, $NO_2$, an unsubstituted $C_1$–$C_4$-alkylendioxy group or one which is mono- to tetra-substituted by $C_1$–$C_4$-alkyl and/or halogen; and $R_5$ is hydrogen.

3. A compound according to claim 2, wherein $R_2$ is $C_1$–$C_6$-alkyl, fluoromethyl, difluoromethyl or 2,2,2-trifluoroethyl;

$R_3$ is $C_1$–$C_6$alkyl, $C_1$–$C_6$-alkoxy, $C_1$–$C_6$-alkoxycarbonyl, CN, $C_3$–$C_6$-cycloalkyl, phenyl which is unsubstituted or mono- to tri-substituted by halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkenyl, $C_2$–$C_4$-alkenyloxy, $C_2$–$C_6$-alkinyl, $C_3$–$C_6$-alkynyloxy, CN, OCN, benzyl, phenyl, or phenyloxy, wherein these aromatic groups are unsubstituted or mono- or disubstituted by halogen, $C_1$–$C_2$-alkyl, $C_1$–$C_2$-haloalkyl or $C_1$–$C_2$-alkoxy.

4. A compound according to claim 3, wherein $R_3$ is $C_1$–$C_4$-alkyl or phenyl, which is unsubstituted or mono- to disubstituted by halogen, $C_1$–$C_2$-alkyl, $C_1$–$C_2$-haloalkyl, $C_1$–$C_2$-alkoxy.

5. An agrochemical composition comprising an effective quantity of a compound of claim 1 and an appropriate carrier.

6. A process for the control of at least one of plant-pathogenic fungi, acarids and insects comprising applying at least one compound of claim 1 to the plant and/or to its locus.

7. The compound of claim 1, wherein $R_3$ represents $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkinyl, $C_2$–$C_6$-alkinyloxy, $C_1$–$C_6$-alkoxycarbonyl or CN, wherein, with the exception of CN, the above-mentioned groups may be substituted by one or more substituents selected from halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylamino-carbonyl, di-$C_1$–$C_6$-alkylaminocarbonyl, $C_2$–$C_6$-alkenyloxy, $C_3$–$C_6$-cycloalkyl, $C_3$–$C_6$-cycloalkoxy, wherein the cyclic radical may be substituted by one or more substituents selected from halogen, cyano, nitro, $C_1$–$C_6$-alkyl, $C_1$–$C_6$-haloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted phenyl, optionally substituted naphthyl, optionally substituted phenyoxy, optionally substituted naphthyloxy.

8. The compound of claim 1, wherein $R_3$ represents phenyl, naphthyl or phenoxy, naphthyloxy, wherein the above-mentioned groups may be substituted by one or more substituted by one or more substituents selected from halogen, $C_1$–$C_6$-alkyl, $C_1$–$C_6$-alkoxy, halo-$C_1$–$C_6$-alkoxy, halo-$C_1$–$C_6$-alkyl, $C_1$–$C_6$-alkylthio, halo-$C_1$–$C_6$-alkylthio, $C_1$–$C_6$-alkylsulfinyl, halo-$C_1$–$C_6$-alkylsulfinyl, $C_1$–$C_6$-alkylsulfonyl, halo-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$-alkylcarbonyl, halo-$C_1$–$C_6$-alkylcarbonyl, $C_1$–$C_6$-alkoxycarbonyl, halo-$C_1$–$C_6$-alkoxycarbonyl, $C_1$–$C_6$-alkylaminocarbonyl, di-($C_1$–$C_6$-alkyl)-aminocarbonyl, $C_1$–$C_6$-alkylaminothiocarbonyl, di-($C_1$–$C_6$-alkyl)-aminothiocarbonyl, $C_1$–$C_6$-alkylamino, di-($C_1$–$C_6$-alkyl)-amino, $NO_2$, an unsubstituted $C_1$–$C_4$-alkylenedioxy group or one which is mono- to tetra-substituted by $C_1$–$C_4$-alkyl and/or by halogen, or CN, $SF_5$ and $QR_4$.

9. The compound of claim 1, wherein $R_3$ is $C_1$–$C_6$alkyl, $C_1$–$C_6$-alkoxy, $C_1$–$C_6$-alkoxycarbonyl, CN, $C_3$–$C_6$-cycloalkyl or phenyl, wherein, with the exception of CN, the above-mentioned groups may be substituted by one or more substituents selected from halogen, $C_1$–$C_6$-alkyl, $C_1$–$C_6$-alkoxy, halo-$C_1$–$C_6$-alkoxy, halo-$C_1$–$C_6$-alkyl, $C_1$–$C_6$-alkylthio, halo-$C_1$–$C_6$-alkylthio, $C_1$–$C_6$-alkylsulfinyl, halo-$C_1$–$C_6$-alkylsulfinyl, $C_1$–$C_6$-alkyl-sulfonyl, halo-$C_1$–$C_6$-alkylsulfonyl, $C_2$–$C_6$-alkenyl, $C_2$–$C_6$-alkenyloxy, $C_2$–$C_6$-alkinyl, $C_3$–$C_6$-alkinyloxy, $C_1$–$C_6$- alkylcarbonyl, halo-$C_1$–$C_6$-alkylcarbonyl, $C_1$–$C_6$-alkoxycarbonyl, halo-$C_1$–$C_6$-alkoxycarbonyl, $C_1$–$C_6$-alkylaminocarbonyl, di-($C_1$–$C_6$-alkyl)-aminocarbonyl, $C_1$–$C_6$-alkylaminothiocarbonyl, di-($C_1$–$C_6$-alkyl)-aminothiocarbonyl, $C_1$–$C_6$-alkylamino, di-($C_1$–$C_6$-alkyl)-amino, $NO_2$, an unsubstituted $C_1$–$C_4$-alkylendioxy group or one which is mono- to tetra-substituted by $C_1$–$C_4$-alkyl and/or halogen.

* * * * *